(12) United States Patent
Schlingensiepen et al.

(10) Patent No.: US 7,667,027 B2
(45) Date of Patent: Feb. 23, 2010

(54) ANTISENSE-OLIGONUCLEOTIDES FOR THE TREATMENT OF IMMUNO-SUPPRESSIVE EFFECTS OF TRANSFORMING GROWTH FACTOR-β (TGF-β)

(75) Inventors: Georg-Ferdinand Schlingensiepen, Gottingen (DE); Wolfgang Brysch, Gottingen (DE); Karl-Hermann Schlingensiepen, Bovenden (DE); Reimar Schlingensiepen, Gottingen (DE); Ulrich Bogdahn, Wurzburg (DE)

(73) Assignee: Biognostik Gesellschaft Fur Biomolekulare Diagnostik mbH, Gottingen (DE)

( * ) Notice: Subject to any disclaimer, the term of this patent is extended or adjusted under 35 U.S.C. 154(b) by 47 days.

(21) Appl. No.: 11/647,586

(22) Filed: Dec. 29, 2006

(65) Prior Publication Data

US 2008/0214483 A1 Sep. 4, 2008

Related U.S. Application Data

(63) Continuation of application No. 10/146,058, filed on May 16, 2002, now abandoned, which is a continuation of application No. 08/535,249, filed as application No. PCT/EP94/01362 on Apr. 29, 1994, now Pat. No. 6,455,689.

(30) Foreign Application Priority Data

Apr. 30, 1993 (EP) .................................. 93107089
May 13, 1993 (EP) .................................. 93107849

(51) Int. Cl.
C07H 21/04 (2006.01)
(52) U.S. Cl. .................................................. 536/24.5
(58) Field of Classification Search .................. 536/24.5
See application file for complete search history.

(56) References Cited

U.S. PATENT DOCUMENTS 5,221,620 A * 6/1993 Purchio et al. ............... 435/360
5,464,945 A 11/1995 Reynolds et al.
5,596,072 A 1/1997 Culpepper et al.

FOREIGN PATENT DOCUMENTS

EP 0293785 12/1988
EP 0433225 6/1991

OTHER PUBLICATIONS

Hatzfeld et al.; "Release of Early Human Hematopoietic Progenitors from Quiescence by Antisense Transforming Growth Factor β1 or Rb Oligonucleotides"; Journal of Experimental Medicine, Oct. 1991; 3 pages; [XP000571050].
Slawomir et al.; "Reversal of Tumor-Induced Immunosuppression: A New Approach to Cancer Therapy"; Journal of Immunotherapy; Feb. 1997; p. 165-177.
Slawomir et al.; "Reversal of tumor-induced immunosuppression by TGF-β inhibitors"; Investigational New Drugs; vol. 21; p. 2-32; 2003.
Boedahn, et al., "Autocrine stimulation of malignant gliomas in vitro by TGF-β: A study with phosphorothioate antisense oligonucleotides," *Proceeding of the Annual Meeting of the American Association for Cancer Research*, 34, 518 (1993), Abstract, ISSN: 0197-016X [XP-002137611 (3091)].
Maxwell et al., "Effect of the expression of transforming growth factor-β2 in primary human glioblastomas on immunosuppression and loss of immune surveillance," *J Neurosurg*, 76, 799-804 (1992) [XP-000907113].
Chai et al., "Specific transforming growth factor-β subtypes regulate embryonic mouse Meckel's cartilage and tooth development," *Developmental Biology*, 162, 85-103 (1994) [XP-000907143].
Tanaka et al., "Synthesis of oligoribonucleotides via the phosphite-triester approach on a polymer support," *Chem. Pharm. Bull.*, 34, 1426-1432 (1986) [XP-002058337].
Jachimczak, et al., "The effect of transforming growth factor-β2-specific phosphorothioate-anti-sense oligodeoxynucleotides in reversing cellular immunosuppression in malignant glioma," *J. Neurosurg*, 78, 944-951 (Jun. 1993) [XP-000886109].
Branch, Tibs, 23:45-50, Feb. 1998.
Ueki et al., Excessive production of transforming growth-factor . . . ; XP-002117560; Biochimica et Biophysica Acta, 1137 (1992) pp. 189-1960.
Martin et al., Complementary DNA for human glioblastoma-derived . . . ; The EMBO Journal, (1987), vol. 6, No. 12, pp. 3673-3677.

* cited by examiner

*Primary Examiner*—Brian Whiteman
(74) *Attorney, Agent, or Firm*—Jacobson Holman PLLC

(57) ABSTRACT

Antisense-oligonucleotides or effective derivatives thereof hybridizing with an area of a gene coding for transforming growth factor-β (TGF-β) comprising the following nucleic acid sequences identified in the sequence listing under SEQ ID NO. 1-56 and 137 or comprising the following nucleic acid sequences identified in the sequence listing under SEQ ID NO. 57 to 136 each of the nucleic acids having a DNA- or RNA-type structure.

2 Claims, 8 Drawing Sheets

Adenine

Guanine

Cytosine

Thymine

Adenine

Guanine

Cytosine

Uracil

Figure 1:
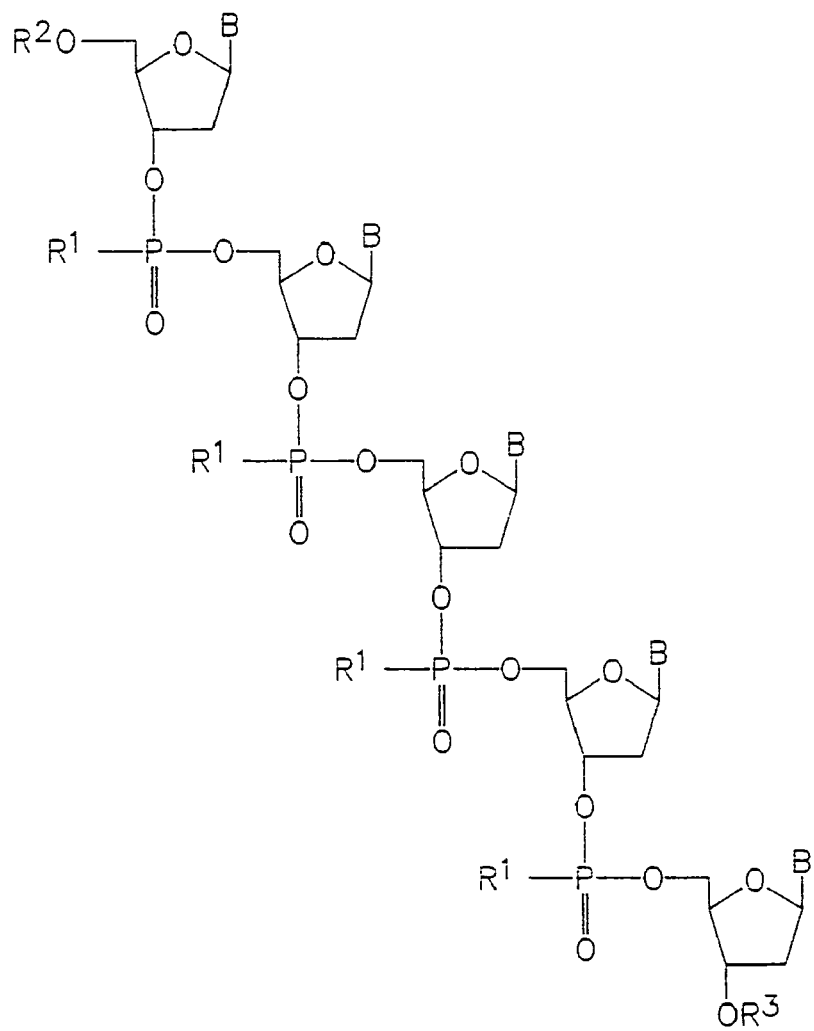
Figure 1:
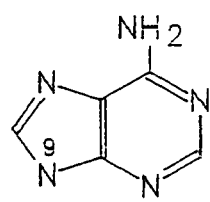
Figure 1:
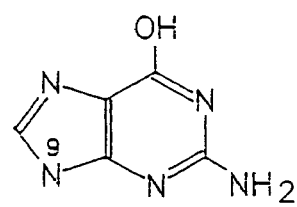
Figure 1:
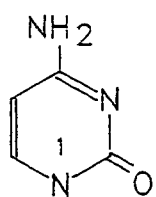
Figure 1:
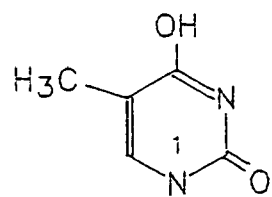

SEQUENCE LISTING

<160> NUMBER OF SEQ ID NOS: 139

<210> SEQ ID NO 1
<211> LENGTH: 14
<212> TYPE: DNA
<213> ORGANISM: artificial
<220> FEATURE:
<223> OTHER INFORMATION: antisense

<400> SEQUENCE: 1
tgcaggtgga tagt                                                            14

<210> SEQ ID NO 2
<211> LENGTH: 18
<212> TYPE: DNA
<213> ORGANISM: artificial
<220> FEATURE:
<223> OTHER INFORMATION: antisense

<400> SEQUENCE: 2
catgtcgata gtcttgca                                                        18

<210> SEQ ID NO 3
<211> LENGTH: 14
<212> TYPE: DNA
<213> ORGANISM: artificial
<220> FEATURE:
<223> OTHER INFORMATION: antisense

<400> SEQUENCE: 3
gtcgatagtc ttgc                                                            14

<210> SEQ ID NO 4
<211> LENGTH: 14
<212> TYPE: DNA
<213> ORGANISM: artificial
<220> FEATURE:
<223> OTHER INFORMATION: antisense

<400> SEQUENCE: 4
ccatgtcgat agtc                                                            14

<210> SEQ ID NO 5
<211> LENGTH: 14
<212> TYPE: DNA
<213> ORGANISM: artificial
<220> FEATURE:
<223> OTHER INFORMATION: antisense

<400> SEQUENCE: 5
ctccatgtcg atag                                                            14

<210> SEQ ID NO 6
<211> LENGTH: 14
<212> TYPE: DNA
<213> ORGANISM: artificial
<220> FEATURE:
<223> OTHER INFORMATION: antisense

<400> SEQUENCE: 6
cttggacagg atct                                                            14

<210> SEQ ID NO 7
<211> LENGTH: 14

```
<212> TYPE: DNA
<213> ORGANISM: artificial
<220> FEATURE:
<223> OTHER INFORMATION: antisense

<400> SEQUENCE: 7
tgctgttgta cagg                                                         14

<210> SEQ ID NO 8
<211> LENGTH: 14
<212> TYPE: DNA
<213> ORGANISM: artificial
<220> FEATURE:
<223> OTHER INFORMATION: antisense

<400> SEQUENCE: 8
gtgctgttgt acag                                                         14

<210> SEQ ID NO 9
<211> LENGTH: 14
<212> TYPE: DNA
<213> ORGANISM: antisense

<400> SEQUENCE: 9
ttggcgtagt agtc                                                         14

<210> SEQ ID NO 10
<211> LENGTH: 14
<212> TYPE: DNA
<213> ORGANISM: artificial
<220> FEATURE:
<223> OTHER INFORMATION: antisense

<400> SEQUENCE: 10
tccaccatta gcac                                                         14

<210> SEQ ID NO 11
<211> LENGTH: 14
<212> TYPE: DNA
<213> ORGANISM: artificial
<220> FEATURE:
<223> OTHER INFORMATION: antisense

<400> SEQUENCE: 11
gatttcgttg tggg                                                         14

<210> SEQ ID NO 12
<211> LENGTH: 18
<212> TYPE: DNA
<213> ORGANISM: artificial
<220> FEATURE:
<223> OTHER INFORMATION: antisense

<400> SEQUENCE: 12
gtcatagatt tcgttgtg                                                     18

<210> SEQ ID NO 13
<211> LENGTH: 16
<212> TYPE: DNA
<213> ORGANISM: antisense

<400> SEQUENCE: 13
tgtactctgc ttgaac                                                       16

<210> SEQ ID NO 14
```

<211> LENGTH: 14
<212> TYPE: DNA
<213> ORGANISM: artificial
<220> FEATURE:
<223> OTHER INFORMATION: antisense

<400> SEQUENCE: 14
gtgtactctg cttg                                                        14

<210> SEQ ID NO 15
<211> LENGTH: 14
<212> TYPE: DNA
<213> ORGANISM: artificial
<220> FEATURE:
<223> OTHER INFORMATION: antisense

<400> SEQUENCE: 15
tgctgtgtgt actc                                                        14

<210> SEQ ID NO 16
<211> LENGTH: 18
<212> TYPE: DNA
<213> ORGANISM: antisense

<400> SEQUENCE: 16
ctgatgtgtt gaagaaca                                                    18

<210> SEQ ID NO 17
<211> LENGTH: 16
<212> TYPE: DNA
<213> ORGANISM: artificial
<220> FEATURE:
<223> OTHER INFORMATION: antisense

<400> SEQUENCE: 17
ctctgatgtg ttgaag                                                      16

<210> SEQ ID NO 18
<211> LENGTH: 14
<212> TYPE: DNA
<213> ORGANISM: artificial
<220> FEATURE:
<223> OTHER INFORMATION: antisense

<400> SEQUENCE: 18
gctctgatgt gttg                                                        14

<210> SEQ ID NO 19
<211> LENGTH: 14
<212> TYPE: DNA
<213> ORGANISM: artificial
<220> FEATURE:
<223> OTHER INFORMATION: antisense

<400> SEQUENCE: 19
gagctctgat gtgt                                                        14

<210> SEQ ID NO 20
<211> LENGTH: 18
<212> TYPE: DNA
<213> ORGANISM: artificial
<220> FEATURE:
<223> OTHER INFORMATION: antisense

<400> SEQUENCE: 20
cacttttaac ttgagcct                                                    18

```
<210> SEQ ID NO 21
<211> LENGTH: 18
<212> TYPE: DNA
<213> ORGANISM: artificial
<220> FEATURE:
<223> OTHER INFORMATION: antisense

<400> SEQUENCE: 21
ctccactttt aacttgag                                                 18

<210> SEQ ID NO 22
<211> LENGTH: 18
<212> TYPE: DNA
<213> ORGANISM: artificial
<220> FEATURE:
<223> OTHER INFORMATION: antisense

<400> SEQUENCE: 22
tgctgtattt ctggtaca                                                 18

<210> SEQ ID NO 23
<211> LENGTH: 14
<212> TYPE: DNA
<213> ORGANISM: artificial
<220> FEATURE:
<223> OTHER INFORMATION: antisense

<400> SEQUENCE: 23
ccaggaattg ttgc                                                     14

<210> SEQ ID NO 24
<211> LENGTH: 14
<212> TYPE: DNA
<213> ORGANISM: artificial
<220> FEATURE:
<223> OTHER INFORMATION: antisense

<400> SEQUENCE: 24
ttgctgaggt atcg                                                     14

<210> SEQ ID NO 25
<211> LENGTH: 14
<212> TYPE: DNA
<213> ORGANISM: artificial
<220> FEATURE:
<223> OTHER INFORMATION: antisense

<400> SEQUENCE: 25
gataaccact ctgg                                                     14

<210> SEQ ID NO 26
<211> LENGTH: 18
<212> TYPE: DNA
<213> ORGANISM: artificial
<220> FEATURE:
<223> OTHER INFORMATION: antisense

<400> SEQUENCE: 26
caaaagataa ccactctg                                                 18

<210> SEQ ID NO 27
<211> LENGTH: 15
<212> TYPE: DNA
<213> ORGANISM: artificial
<220> FEATURE:
```

-continued

```
<223> OTHER INFORMATION: antisense

<400> SEQUENCE: 27
cggtgacatc aaaag                                                    15

<210> SEQ ID NO 28
<211> LENGTH: 14
<212> TYPE: DNA
<213> ORGANISM: artificial
<220> FEATURE:
<223> OTHER INFORMATION: antisense

<400> SEQUENCE: 28
cctcaatttc ccct                                                     14

<210> SEQ ID NO 29
<211> LENGTH: 14
<212> TYPE: DNA
<213> ORGANISM: artificial
<220> FEATURE:
<223> OTHER INFORMATION: antisense

<400> SEQUENCE: 29
gttatccctg ctgt                                                     14

<210> SEQ ID NO 30
<211> LENGTH: 14
<212> TYPE: DNA
<213> ORGANISM: artificial
<220> FEATURE:
<223> OTHER INFORMATION: antisense

<400> SEQUENCE: 30
gcagtgtgtt atcc                                                     14

<210> SEQ ID NO 31
<211> LENGTH: 14
<212> TYPE: DNA
<213> ORGANISM: artificial
<220> FEATURE:
<223> OTHER INFORMATION: antisense

<400> SEQUENCE: 31
gatgtccact tgca                                                     14

<210> SEQ ID NO 32
<211> LENGTH: 14
<212> TYPE: DNA
<213> ORGANISM: artificial
<220> FEATURE:
<223> OTHER INFORMATION: antisense

<400> SEQUENCE: 32
tagtgaaccc gttg                                                     14

<210> SEQ ID NO 33
<211> LENGTH: 14
<212> TYPE: DNA
<213> ORGANISM: artificial
<220> FEATURE:
<223> OTHER INFORMATION: antisense

<400> SEQUENCE: 33
tgccatgaat ggtg                                                     14
```

```
<210> SEQ ID NO 34
<211> LENGTH: 16
<212> TYPE: DNA
<213> ORGANISM: artificial
<220> FEATURE:
<223> OTHER INFORMATION: antisense

<400> SEQUENCE: 34
gttcatgcca tgaatg                                                    16

<210> SEQ ID NO 35
<211> LENGTH: 14
<212> TYPE: DNA
<213> ORGANISM: artificial
<220> FEATURE:
<223> OTHER INFORMATION: antisense

<400> SEQUENCE: 35
catgagaagc agga                                                      14

<210> SEQ ID NO 36
<211> LENGTH: 14
<212> TYPE: DNA
<213> ORGANISM: artificial
<220> FEATURE:
<223> OTHER INFORMATION: antisense

<400> SEQUENCE: 36
gctttgcaga tgct                                                      14

<210> SEQ ID NO 37
<211> LENGTH: 14
<212> TYPE: DNA
<213> ORGANISM: artificial
<220> FEATURE:
<223> OTHER INFORMATION: antisense

<400> SEQUENCE: 37
gagctttgca gatg                                                      14

<210> SEQ ID NO 38
<211> LENGTH: 14
<212> TYPE: DNA
<213> ORGANISM: antisense

<400> SEQUENCE: 38
tagttggtgt ccag                                                      14

<210> SEQ ID NO 39
<211> LENGTH: 16
<212> TYPE: DNA
<213> ORGANISM: artificial
<220> FEATURE:
<223> OTHER INFORMATION: antisense

<400> SEQUENCE: 39
ctgaagcaat agttgg                                                    16

<210> SEQ ID NO 40
<211> LENGTH: 18
<212> TYPE: DNA
<213> ORGANISM: artificial
<220> FEATURE:
<223> OTHER INFORMATION: antisense

<400> SEQUENCE: 40
```

| | |
|---|---|
| agctgaagca atagttgg | 18 |

```
<210> SEQ ID NO 41
<211> LENGTH: 14
<212> TYPE: DNA
<213> ORGANISM: artificial
<220> FEATURE:
<223> OTHER INFORMATION: antisense

<400> SEQUENCE: 41
```

| | |
|---|---|
| ggagctgaag caat | 14 |

```
<210> SEQ ID NO 42
<211> LENGTH: 14
<212> TYPE: DNA
<213> ORGANISM: artificial
<220> FEATURE:
<223> OTHER INFORMATION: antisense

<400> SEQUENCE: 42
```

| | |
|---|---|
| caatgtacag ctgc | 14 |

```
<210> SEQ ID NO 43
<211> LENGTH: 16
<212> TYPE: DNA
<213> ORGANISM: artificial
<220> FEATURE:
<223> OTHER INFORMATION: antisense

<400> SEQUENCE: 43
```

| | |
|---|---|
| ggaagtcaat gtacag | 16 |

```
<210> SEQ ID NO 44
<211> LENGTH: 15
<212> TYPE: DNA
<213> ORGANISM: artificial
<220> FEATURE:
<223> OTHER INFORMATION: antisense

<400> SEQUENCE: 44
```

| | |
|---|---|
| cggaagtcaa tgtac | 15 |

```
<210> SEQ ID NO 45
<211> LENGTH: 14
<212> TYPE: DNA
<213> ORGANISM: artificial
<220> FEATURE:
<223> OTHER INFORMATION: antisense

<400> SEQUENCE: 45
```

| | |
|---|---|
| gcggaagtca atgt | 14 |

```
<210> SEQ ID NO 46
<211> LENGTH: 14
<212> TYPE: DNA
<213> ORGANISM: artificial
<220> FEATURE:
<223> OTHER INFORMATION: antisense

<400> SEQUENCE: 46
```

| | |
|---|---|
| agttggcatg gtag | 14 |

```
<210> SEQ ID NO 47
<211> LENGTH: 14
<212> TYPE: DNA
<213> ORGANISM: artificial
```

```
<220> FEATURE:
<223> OTHER INFORMATION: antisense

<400> SEQUENCE: 47
gcagaagttg gcat                                                    14

<210> SEQ ID NO 48
<211> LENGTH: 14
<212> TYPE: DNA
<213> ORGANISM: artificial
<220> FEATURE:
<223> OTHER INFORMATION: antisense

<400> SEQUENCE: 48
ctccaaatgt aggg                                                    14

<210> SEQ ID NO 49
<211> LENGTH: 14
<212> TYPE: DNA
<213> ORGANISM: artificial
<220> FEATURE:
<223> OTHER INFORMATION: antisense

<400> SEQUENCE: 49
accttgctgt actg                                                    14

<210> SEQ ID NO 50
<211> LENGTH: 14
<212> TYPE: DNA
<213> ORGANISM: artificial
<220> FEATURE:
<223> OTHER INFORMATION: antisense

<400> SEQUENCE: 50
tgctggttgt acag                                                    14

<210> SEQ ID NO 51
<211> LENGTH: 14
<212> TYPE: DNA
<213> ORGANISM: artificial
<220> FEATURE:
<223> OTHER INFORMATION: antisense

<400> SEQUENCE: 51
ggttatgctg gttg                                                    14

<210> SEQ ID NO 52
<211> LENGTH: 14
<212> TYPE: DNA
<213> ORGANISM: artificial
<220> FEATURE:
<223> OTHER INFORMATION: antisense

<400> SEQUENCE: 52
gtagtacacg atgg                                                    14

<210> SEQ ID NO 53
<211> LENGTH: 14
<212> TYPE: DNA
<213> ORGANISM: artificial
<220> FEATURE:
<223> OTHER INFORMATION: antisense

<400> SEQUENCE: 53
cgtagtacac gatg                                                    14
```

```
<210> SEQ ID NO 54
<211> LENGTH: 14
<212> TYPE: DNA
<213> ORGANISM: antisense

<400> SEQUENCE: 54
cacgtagtac acga                                                         14

<210> SEQ ID NO 55
<211> LENGTH: 14
<212> TYPE: DNA
<213> ORGANISM: artificial
<220> FEATURE:
<223> OTHER INFORMATION: antisense

<400> SEQUENCE: 55
catgttggac agct                                                         14

<210> SEQ ID NO 56
<211> LENGTH: 14
<212> TYPE: DNA
<213> ORGANISM: artificial
<220> FEATURE:
<223> OTHER INFORMATION: antisense

<400> SEQUENCE: 56
gcacgatcat gttg                                                         14

<210> SEQ ID NO 57
<211> LENGTH: 14
<212> TYPE: DNA
<213> ORGANISM: artificial
<220> FEATURE:
<223> OTHER INFORMATION: antisense

<400> SEQUENCE: 57
cacacagtag tgca                                                         14

<210> SEQ ID NO 58
<211> LENGTH: 14
<212> TYPE: DNA
<213> ORGANISM: artificial
<220> FEATURE:
<223> OTHER INFORMATION: antisense

<400> SEQUENCE: 58
gatcagaaaa gcgc                                                         14

<210> SEQ ID NO 59
<211> LENGTH: 14
<212> TYPE: DNA
<213> ORGANISM: artificial
<220> FEATURE:
<223> OTHER INFORMATION: antisense

<400> SEQUENCE: 59
accgtgacca gatg                                                         14

<210> SEQ ID NO 60
<211> LENGTH: 14
<212> TYPE: DNA
<213> ORGANISM: artificial
<220> FEATURE:
<223> OTHER INFORMATION: antisense

<400> SEQUENCE: 60
```

```
gtagacaggc tgag                                                    14

<210> SEQ ID NO 61
<211> LENGTH: 14
<212> TYPE: DNA
<213> ORGANISM: artificial
<220> FEATURE:
<223> OTHER INFORMATION: antisense

<400> SEQUENCE: 61
tatcgagtgt gctg                                                    14

<210> SEQ ID NO 62
<211> LENGTH: 14
<212> TYPE: DNA
<213> ORGANISM: artificial
<220> FEATURE:
<223> OTHER INFORMATION: antisense

<400> SEQUENCE: 62
ttgcgcatga actg                                                    14

<210> SEQ ID NO 63
<211> LENGTH: 14
<212> TYPE: DNA
<213> ORGANISM: antisense

<400> SEQUENCE: 63
ttgctcagga tctg                                                    14

<210> SEQ ID NO 64
<211> LENGTH: 14
<212> TYPE: DNA
<213> ORGANISM: artificial
<220> FEATURE:
<223> OTHER INFORMATION: antisense

<400> SEQUENCE: 64
actggtgagc ttca                                                    14

<210> SEQ ID NO 65
<211> LENGTH: 14
<212> TYPE: DNA
<213> ORGANISM: artificial
<220> FEATURE:
<223> OTHER INFORMATION: antisense

<400> SEQUENCE: 65
atagtcttct gggg                                                    14

<210> SEQ ID NO 66
<211> LENGTH: 14
<212> TYPE: DNA
<213> ORGANISM: artificial
<220> FEATURE:
<223> OTHER INFORMATION: antisense

<400> SEQUENCE: 66
gctcaggata gtct                                                    14

<210> SEQ ID NO 67
<211> LENGTH: 18
<212> TYPE: DNA
<213> ORGANISM: artificial
<220> FEATURE:
```

<223> OTHER INFORMATION: antisense

<400> SEQUENCE: 67
tgtagatgga aatcacct                                              18

<210> SEQ ID NO 68
<211> LENGTH: 14
<212> TYPE: DNA
<213> ORGANISM: artificial
<220> FEATURE:
<223> OTHER INFORMATION: antisense

<400> SEQUENCE: 68
tggtgctgtt gtag                                                  14

<210> SEQ ID NO 69
<211> LENGTH: 14
<212> TYPE: DNA
<213> ORGANISM: artificial
<220> FEATURE:
<223> OTHER INFORMATION: antisense

<400> SEQUENCE: 69
ttctcctgga gcaa                                                  14

<210> SEQ ID NO 70
<211> LENGTH: 14
<212> TYPE: DNA
<213> ORGANISM: artificial
<220> FEATURE:
<223> OTHER INFORMATION: antisense

<400> SEQUENCE: 70
tactcttcgt cgct                                                  14

<210> SEQ ID NO 71
<211> LENGTH: 14
<212> TYPE: DNA
<213> ORGANISM: artificial
<220> FEATURE:
<223> OTHER INFORMATION: antisense

<400> SEQUENCE: 71
cttggcgtag tact                                                  14

<210> SEQ ID NO 72
<211> LENGTH: 18
<212> TYPE: DNA
<213> ORGANISM: artificial
<220> FEATURE:
<223> OTHER INFORMATION: antisense

<400> SEQUENCE: 72
cggcatgtct attttgta                                              18

<210> SEQ ID NO 73
<211> LENGTH: 14
<212> TYPE: DNA
<213> ORGANISM: artificial
<220> FEATURE:
<223> OTHER INFORMATION: antisense

<400> SEQUENCE: 73
ttttcggagg ggaa                                                  14

<210> SEQ ID NO 74
<211> LENGTH: 14
<212> TYPE: DNA
<213> ORGANISM: artificial
<220> FEATURE:
<223> OTHER INFORMATION: antisense

<400> SEQUENCE: 74
cgggatggca tttt                                                       14

<210> SEQ ID NO 75
<211> LENGTH: 14
<212> TYPE: DNA
<213> ORGANISM: artificial
<220> FEATURE:
<223> OTHER INFORMATION: antisense

<400> SEQUENCE: 75
ctgtagaaag tggg                                                       14

<210> SEQ ID NO 76
<211> LENGTH: 18
<212> TYPE: DNA
<213> ORGANISM: artificial
<220> FEATURE:
<223> OTHER INFORMATION: antisense

<400> SEQUENCE: 76
acaattctga agtagggt                                                   18

<210> SEQ ID NO 77
<211> LENGTH: 18
<212> TYPE: DNA
<213> ORGANISM: artificial
<220> FEATURE:
<223> OTHER INFORMATION: antisense

<400> SEQUENCE: 77
attgctgaga cgtcaaat                                                   18

<210> SEQ ID NO 78
<211> LENGTH: 14
<212> TYPE: DNA
<213> ORGANISM: artificial
<220> FEATURE:
<223> OTHER INFORMATION: antisense

<400> SEQUENCE: 78
tctccattgc tgag                                                       14

<210> SEQ ID NO 79
<211> LENGTH: 18
<212> TYPE: DNA
<213> ORGANISM: artificial
<220> FEATURE:
<223> OTHER INFORMATION: antisense

<400> SEQUENCE: 79
tcaccaaatt ggaagcat                                                   18

<210> SEQ ID NO 80
<211> LENGTH: 14
<212> TYPE: DNA
<213> ORGANISM: artificial
<220> FEATURE:
<223> OTHER INFORMATION: antisense

```
<400> SEQUENCE: 80
ctctgaactc tgct                                                         14

<210> SEQ ID NO 81
<211> LENGTH: 18
<212> TYPE: DNA
<213> ORGANISM: artificial
<220> FEATURE:
<223> OTHER INFORMATION: antisense

<400> SEQUENCE: 81
aacgaaagac tctgaact                                                     18

<210> SEQ ID NO 82
<211> LENGTH: 14
<212> TYPE: DNA
<213> ORGANISM: artificial
<220> FEATURE:
<223> OTHER INFORMATION: antisense

<400> SEQUENCE: 82
tgggttctgc aaac                                                         14

<210> SEQ ID NO 83
<211> LENGTH: 14
<212> TYPE: DNA
<213> ORGANISM: artificial
<220> FEATURE:
<223> OTHER INFORMATION: antisense

<400> SEQUENCE: 83
ctggcttttg ggtt                                                         14

<210> SEQ ID NO 84
<211> LENGTH: 14
<212> TYPE: DNA
<213> ORGANISM: artificial
<220> FEATURE:
<223> OTHER INFORMATION: antisense

<400> SEQUENCE: 84
gttgttcagg cact                                                         14

<210> SEQ ID NO 85
<211> LENGTH: 18
<212> TYPE: DNA
<213> ORGANISM: antisense

<400> SEQUENCE: 85
tctgatatag ctcaatcc                                                     18

<210> SEQ ID NO 86
<211> LENGTH: 18
<212> TYPE: DNA
<213> ORGANISM: artificial
<220> FEATURE:
<223> OTHER INFORMATION: antisense

<400> SEQUENCE: 86
tctttggact tgagaatc                                                     18

<210> SEQ ID NO 87
<211> LENGTH: 14
<212> TYPE: DNA
<213> ORGANISM: artificial
```

```
<220> FEATURE:
<223> OTHER INFORMATION: antisense

<400> SEQUENCE: 87
tgggttggag atgt                                                        14

<210> SEQ ID NO 88
<211> LENGTH: 14
<212> TYPE: DNA
<213> ORGANISM: antisense

<400> SEQUENCE: 88
tgctgtcgat gtag                                                        14

<210> SEQ ID NO 89
<211> LENGTH: 16
<212> TYPE: DNA
<213> ORGANISM: artificial
<220> FEATURE:
<223> OTHER INFORMATION: antisense

<400> SEQUENCE: 89
acaactttgc tgtcga                                                      16

<210> SEQ ID NO 90
<211> LENGTH: 14
<212> TYPE: DNA
<213> ORGANISM: artificial
<220> FEATURE:
<223> OTHER INFORMATION: antisense

<400> SEQUENCE: 90
attcgccttc tgct                                                        14

<210> SEQ ID NO 91
<211> LENGTH: 14
<212> TYPE: DNA
<213> ORGANISM: artificial
<220> FEATURE:
<223> OTHER INFORMATION: antisense

<400> SEQUENCE: 91
gaaggagagc catt                                                        14

<210> SEQ ID NO 92
<211> LENGTH: 16
<212> TYPE: DNA
<213> ORGANISM: antisense

<400> SEQUENCE: 92
tcagttacat cgaagg                                                      16

<210> SEQ ID NO 93
<211> LENGTH: 18
<212> TYPE: DNA
<213> ORGANISM: artificial
<220> FEATURE:
<223> OTHER INFORMATION: antisense

<400> SEQUENCE: 93
tgaagccatt catgaaca                                                    18

<210> SEQ ID NO 94
<211> LENGTH: 16
<212> TYPE: DNA
```

```
<213> ORGANISM: artificial
<220> FEATURE:
<223> OTHER INFORMATION: antisense

<400> SEQUENCE: 94
tcctgtcttt atggtg                                                      16

<210> SEQ ID NO 95
<211> LENGTH: 14
<212> TYPE: DNA
<213> ORGANISM: artificial
<220> FEATURE:
<223> OTHER INFORMATION: antisense

<400> SEQUENCE: 95
aaatcccagg ttcc                                                        14

<210> SEQ ID NO 96
<211> LENGTH: 18
<212> TYPE: DNA
<213> ORGANISM: artificial
<220> FEATURE:
<223> OTHER INFORMATION: antisense

<400> SEQUENCE: 96
ggacagtgta agcttatt                                                    18

<210> SEQ ID NO 97
<211> LENGTH: 16
<212> TYPE: DNA
<213> ORGANISM: artificial
<220> FEATURE:
<223> OTHER INFORMATION: antisense

<400> SEQUENCE: 97
gtacaaaagt gcagca                                                      16

<210> SEQ ID NO 98
<211> LENGTH: 18
<212> TYPE: DNA
<213> ORGANISM: artificial
<220> FEATURE:
<223> OTHER INFORMATION: antisense

<400> SEQUENCE: 98
tagatggtac aaaagtgc                                                    18

<210> SEQ ID NO 99
<211> LENGTH: 20
<212> TYPE: DNA
<213> ORGANISM: artificial
<220> FEATURE:
<223> OTHER INFORMATION: antisense

<400> SEQUENCE: 99
cacttttatt tgggatgatg                                                  20

<210> SEQ ID NO 100
<211> LENGTH: 18
<212> TYPE: DNA
<213> ORGANISM: artificial
<220> FEATURE:
<223> OTHER INFORMATION: antisense

<400> SEQUENCE: 100
gcaaatcttg cttctagt                                                    18
```

<210> SEQ ID NO 101
<211> LENGTH: 14
<212> TYPE: DNA
<213> ORGANISM: artificial
<220> FEATURE:
<223> OTHER INFORMATION: antisense

<400> SEQUENCE: 101
gtgccatcaa tacc                                                        14

<210> SEQ ID NO 102
<211> LENGTH: 14
<212> TYPE: DNA
<213> ORGANISM: artificial
<220> FEATURE:
<223> OTHER INFORMATION: antisense

<400> SEQUENCE: 102
ggtatatgtg gagg                                                        14

<210> SEQ ID NO 103
<211> LENGTH: 14
<212> TYPE: DNA
<213> ORGANISM: artificial
<220> FEATURE:
<223> OTHER INFORMATION: antisense

<400> SEQUENCE: 103
tctgatcacc actg                                                       014

<210> SEQ ID NO 104
<211> LENGTH: 18
<212> TYPE: DNA
<213> ORGANISM: artificial
<220> FEATURE:
<223> OTHER INFORMATION: antisense

<400> SEQUENCE: 104
tcctagtgga ctttatag                                                    18

<210> SEQ ID NO 105
<211> LENGTH: 16
<212> TYPE: DNA
<213> ORGANISM: artificial
<220> FEATURE:
<223> OTHER INFORMATION: antisense

<400> SEQUENCE: 105
tttttcctag tggact                                                      16

<210> SEQ ID NO 106
<211> LENGTH: 14
<212> TYPE: DNA
<213> ORGANISM: artificial
<220> FEATURE:
<223> OTHER INFORMATION: antisense

<400> SEQUENCE: 106
agatgtgggg tctt                                                        14

<210> SEQ ID NO 107
<211> LENGTH: 16
<212> TYPE: DNA
<213> ORGANISM: artificial
<220> FEATURE:

<223> OTHER INFORMATION: antisense

<400> SEQUENCE: 107
caataacatt agcagg                                                        16

<210> SEQ ID NO 108
<211> LENGTH: 14
<212> TYPE: DNA
<213> ORGANISM: artificial
<220> FEATURE:
<223> OTHER INFORMATION: antisense

<400> SEQUENCE: 108
aagtctgtag gagg                                                          14

<210> SEQ ID NO 109
<211> LENGTH: 16
<212> TYPE: DNA
<213> ORGANISM: artificial
<220> FEATURE:
<223> OTHER INFORMATION: antisense

<400> SEQUENCE: 109
tctgttgtga ctcaag                                                        16

<210> SEQ ID NO 110
<211> LENGTH: 14
<212> TYPE: DNA
<213> ORGANISM: artificial
<220> FEATURE:
<223> OTHER INFORMATION: antisense

<400> SEQUENCE: 110
gttggtctgt tgtg                                                          14

<210> SEQ ID NO 111
<211> LENGTH: 14
<212> TYPE: DNA
<213> ORGANISM: artificial
<220> FEATURE:
<223> OTHER INFORMATION: antisense

<400> SEQUENCE: 111
caaagcacgc ttct                                                          14

<210> SEQ ID NO 112
<211> LENGTH: 18
<212> TYPE: DNA
<213> ORGANISM: artificial
<220> FEATURE:
<223> OTHER INFORMATION: antisense

<400> SEQUENCE: 112
tttctaaagc aataggcc                                                      18

<210> SEQ ID NO 113
<211> LENGTH: 16
<212> TYPE: DNA
<213> ORGANISM: antisense

<400> SEQUENCE: 113
gcaattatcc tgcaca                                                        16

<210> SEQ ID NO 114
<211> LENGTH: 14

```
<212> TYPE: DNA
<213> ORGANISM: artificial
<220> FEATURE:
<223> OTHER INFORMATION: antisense

<400> SEQUENCE: 114
acgtaggcag caat                                                        14

<210> SEQ ID NO 115
<211> LENGTH: 18
<212> TYPE: DNA
<213> ORGANISM: artificial
<220> FEATURE:
<223> OTHER INFORMATION: antisense

<400> SEQUENCE: 115
atcaatgtaa agtggacg                                                    18

<210> SEQ ID NO 116
<211> LENGTH: 14
<212> TYPE: DNA
<213> ORGANISM: artificial
<220> FEATURE:
<223> OTHER INFORMATION: antisense

<400> SEQUENCE: 116
ctagatccct cttg                                                        14

<210> SEQ ID NO 117
<211> LENGTH: 14
<212> TYPE: DNA
<213> ORGANISM: artificial
<220> FEATURE:
<223> OTHER INFORMATION: antisense

<400> SEQUENCE: 117
ccatttccac ccta                                                        14

<210> SEQ ID NO 118
<211> LENGTH: 14
<212> TYPE: DNA
<213> ORGANISM: artificial
<220> FEATURE:
<223> OTHER INFORMATION: antisense

<400> SEQUENCE: 118
tgggttcgtg tatc                                                        14

<210> SEQ ID NO 119
<211> LENGTH: 14
<212> TYPE: DNA
<213> ORGANISM: artificial
<220> FEATURE:
<223> OTHER INFORMATION: antisense

<400> SEQUENCE: 119
tggcattgta ccct                                                        14

<210> SEQ ID NO 120
<211> LENGTH: 14
<212> TYPE: DNA
<213> ORGANISM: artificial
<220> FEATURE:
<223> OTHER INFORMATION: antisense

<400> SEQUENCE: 120
```

```
tccagcacag aagt                                                        14

<210> SEQ ID NO 121
<211> LENGTH: 16
<212> TYPE: DNA
<213> ORGANISM: antisense

<400> SEQUENCE: 121
ataaatacgg gcatgc                                                      16

<210> SEQ ID NO 122
<211> LENGTH: 14
<212> TYPE: DNA
<213> ORGANISM: artificial
<220> FEATURE:
<223> OTHER INFORMATION: antisense

<400> SEQUENCE: 122
agtgtctgaa ctcc                                                        14

<210> SEQ ID NO 123
<211> LENGTH: 14
<212> TYPE: DNA
<213> ORGANISM: artificial
<220> FEATURE:
<223> OTHER INFORMATION: antisense

<400> SEQUENCE: 123
tgtgctgagt gtct                                                        14

<210> SEQ ID NO 124
<211> LENGTH: 14
<212> TYPE: DNA
<213> ORGANISM: artificial
<220> FEATURE:
<223> OTHER INFORMATION: antisense

<400> SEQUENCE: 124
ataagctcag gacc                                                        14

<210> SEQ ID NO 125
<211> LENGTH: 14
<212> TYPE: DNA
<213> ORGANISM: artificial
<220> FEATURE:
<223> OTHER INFORMATION: antisense

<400> SEQUENCE: 125
aggagaagca gatg                                                        14

<210> SEQ ID NO 126
<211> LENGTH: 14
<212> TYPE: DNA
<213> ORGANISM: artificial
<220> FEATURE:
<223> OTHER INFORMATION: antisense

<400> SEQUENCE: 126
agcaaggaga agca                                                        14

<210> SEQ ID NO 127
<211> LENGTH: 14
<212> TYPE: DNA
<213> ORGANISM: artificial
<220> FEATURE:
<223> OTHER INFORMATION: antisense
```

<400> SEQUENCE: 127
aatcttggga cacg                                                    14

<210> SEQ ID NO 128
<211> LENGTH: 18
<212> TYPE: DNA
<213> ORGANISM: artificial
<220> FEATURE:
<223> OTHER INFORMATION: antisense

<400> SEQUENCE: 128
tagagaatgg ttagaggt                                                18

<210> SEQ ID NO 129
<211> LENGTH: 18
<212> TYPE: DNA
<213> ORGANISM: artificial
<220> FEATURE:
<223> OTHER INFORMATION: antisense

<400> SEQUENCE: 129
gttttgccaa tgtagtag                                                18

<210> SEQ ID NO 130
<211> LENGTH: 14
<212> TYPE: DNA
<213> ORGANISM: artificial
<220> FEATURE:
<223> OTHER INFORMATION: antisense

<400> SEQUENCE: 130
cttgggtgtt ttgc                                                    14

<210> SEQ ID NO 131
<211> LENGTH: 16
<212> TYPE: DNA
<213> ORGANISM: artificial
<220> FEATURE:
<223> OTHER INFORMATION: antisense

<400> SEQUENCE: 131
gcaagacttt acaatc                                                  16

<210> SEQ ID NO 132
<211> LENGTH: 18
<212> TYPE: DNA
<213> ORGANISM: artificial
<220> FEATURE:
<223> OTHER INFORMATION: antisense

<400> SEQUENCE: 132
gcatttgcaa gactttac                                                18

<210> SEQ ID NO 133
<211> LENGTH: 18
<212> TYPE: DNA
<213> ORGANISM: artificial
<220> FEATURE:
<223> OTHER INFORMATION: antisense

<400> SEQUENCE: 133
tttagctgca tttgcaag                                                18

<210> SEQ ID NO 134

```
<211> LENGTH: 14
<212> TYPE: DNA
<213> ORGANISM: artificial
<220> FEATURE:
<223> OTHER INFORMATION: antisense

<400> SEQUENCE: 134 gccactttc caag                                                         14

<210> SEQ ID NO 135
<211> LENGTH: 14
<212> TYPE: DNA
<213> ORGANISM: artificial
<220> FEATURE:
<223> OTHER INFORMATION: antisense

<400> SEQUENCE: 135
ttggtcttgc cact                                                        14

<210> SEQ ID NO 136
<211> LENGTH: 14
<212> TYPE: DNA
<213> ORGANISM: artificial
<220> FEATURE:
<223> OTHER INFORMATION: antisense

<400> SEQUENCE: 136
cagcacacag tagt                                                        14

<210> SEQ ID NO 137
<211> LENGTH: 14
<212> TYPE: DNA
<213> ORGANISM: artificial
<220> FEATURE:
<223> OTHER INFORMATION: antisense

<400> SEQUENCE: 137
cgatagtctt gcag                                                        14

<210> SEQ ID NO 138
<211> LENGTH: 14
<212> TYPE: DNA
<213> ORGANISM: artificial
<220> FEATURE:
<223> OTHER INFORMATION: antisense

<400> SEQUENCE: 138
cagcacacag tact                                                        14

<210> SEQ ID NO 139
<211> LENGTH: 14
<212> TYPE: DNA
<213> ORGANISM: artificial
<220> FEATURE:
<223> OTHER INFORMATION: antisense

<400> SEQUENCE: 139
gtccctatac gaac                                                        14
```

ANTISENSE-OLIGONUCLEOTIDES FOR THE TREATMENT OF IMMUNO-SUPPRESSIVE EFFECTS OF TRANSFORMING GROWTH FACTOR-β (TGF-β)

This is a continuation of Ser. No. 10/146,058, filed, May 16, 2002 (abandoned), which is a continuation of Ser. No. 08/535,249, filed, Oct. 30, 1995 (now U.S. Pat. No. 6,455,689), which is a 371 of PCT/EP94/01362, filed Apr. 29, 1994.

The present invention is related to antisense-oligonucleotides or effective derivatives thereof hybridizing with an area of a gene coding for transforming growth factor-β (TGF-β), oligonucleotides as nonsense control nucleotides, a pharmaceutical composition comprising at least one antisense-oligonucleotide or effective derivatives thereof hybridizing with an area of a gene coding for TGF-β as well as a use of antisense-oligonucleotides for the manufacturing of a pharmaceutical composition for the treatment of tumors and/or the treatment of the immunosuppressive effect of TGF-β.

The transforming growth factor-β (TGF-β) is a factor which is, for example, secreted by human glioma cells. Human gliomas such as alioblastoma are human tumors for which at present no satisfactory therapy exists. The TGF-β supports in an autocrine manner the growing of the respective tumor cells. The factor shows immunosuppressive effects and reduces (the proliferation of such cytotoxic T-lymphocytes which otherwise would be able to destroy the glioma cells.

The suppression of immune responsiveness has been well documented in patients with malignant gliomas. These patients express a variety of immunological deficiencies including cutaneous anergy, depressed antibody production, diminished numbers of circulating T-cells (Brooks, W. H., Netsky, M. G., Horwitz, D. A., Normansell, D. E. Cell mediated immunity in patients with primary brain tumors, J. Exp. Med., 136: 1931-1947, 1972 and Roszman, T., Elliott, L., Brooks, W. Modulation of T-cell function by gliomas, Immunol. Today 12: 370-374, 1991). More recent studies indicate that these impairments may result from malfunctions in physiological pathways required for normal T-cell activation and from quantitative and qualitative defects in T-cell subsets.

In Proceedings of the 82nd Annual meeting of the American Association for Cancer Research, Houston Tex., USA, May 15-18, 1991, Proc AM ASSOC CANCER RES ANNU MEET 32 (O), 1991, 427 is disclosed that factor-β-antisense-oligonucleotides inhibit a human melanoma cell line under serum-enriched and stimulate under serum-free culture conditions. The results established indicate different roles of cellular TGF-$\beta_1$ in the growth regulation of HTZ-19-cells depending on the amount of serum present in the culture medium. In addition this may indicate the biological potential and possible draw-backs of exogenously administered TGF-β-antisense.

J. EXP. MED. 174 (4), 1991, 925-930, Hatzfield J. et al, "Release of early human hematopoietic progenitors from quiescence by antisense transforming growth factor β-1 or Rb oligonucleotides" discloses release of early human hematopoietic progenitors from quiescence by antisense transforming growth factor β1 or Rb oligonucleotides. Rb antisense TGF-β negatively regulates the cycling status of early hematopoietic progenitors through interaction with the Rb gene product.

Proceedings of the National Academy of Sciences of USA, Vo. 88, February 1991, Washington US, pages 1516-1520, Potts, J. et al., "Epithelial-mesenchymal transformation of embryonic cardiac antisense oligodeoxynucleotide to transforming growth factor beta 3'" discloses that epithelial-mesenchymal transformation of embryonic cardiac endothelial cells is inhibited by a modified antisense oligodeoxynucleotide to transforming growth factor β3. The transformation depends on the activity of a transforming growth factor β (TGF-β) molecule produced by the heart. Modified antisense oligodeoxynucleotides generated to non-conserved regions of TGF-β1, -2, -3 and -4 were prepared in order to examine the possible roles of these members in this transformation. As a result it has been shown that a specific member of the TGF-β family (TGF-β3) is essential for the epithelial-mesenchymal transformation.

WO-A 92/17206 discloses a composition for use in the treatment of wounds to inhibit scar tissue formation during healing comprising an effective activity-inhibitor amount of a growth factor neutralising agent or agents specific against only fibrotic growth factors together with a pharmaceutically acceptable carrier. The method of preparation of said composition and method of administering the composition to a host suffering from tissue wounding is also disclosed.

WO-A 90/09180 discloses methods useful in autologous bone marrow transplantation and cancer therapy. Bone marrow cells from a patient having cancer are treated with selected antisense oligonucleotides in order to deplete the bone marrow of malignant cells prior to infusion back into the bone marrow donor.

It is an object of the present invention to provide a method for the treatment of cancer cells which are correlated with an immunosuppression. Another object of the present invention is to provide an effective agent which inhibits the growth of tumor cells which are related to an immunosuppression.

According to the invention antisense-oligonucleotides or effective derivatives thereof which hybridizes with an area of gene region coding for transforming growth factor-β (TGF-β) comprising the following nucleic acid sequences identified in the sequence listing under SEQ ID NO. 1-56 and 137 or comprising the following nucleic acid sequences identified in the sequence listing under SEQ ID NO. 57 to 136 each of the nucleic acids having a DNA- or RNA-type structure are able to solve the problems addressed above. Preferably, the antisense-oligonucleotides hybridize with an area of a gene region coding for growth factor-$\beta_1$, -$\beta_2$ and/or $\beta_3$. The antisense-oligonucleotide is either able to hybridize with areas of a gene region coding for TGF-β and/or areas of a gene region coding and non coding for TGF-β. For example, some nucleotides of the antisense-oligonucleotide sequence hybridizing with an area of a gene region coding for transforming growth factor-β is hybridizing with an area which does not code for the transforming growth factor whereas, the other part of the respective sequence does hybridize with a gene region coding for TGF-β. Of course, it is also in the scope of the present invention that the antisense-oligonucleotide hybridizes with an area of a gene region just coding for growth factor-β. It is also understood by the skilled person that fragments having subsequences of the antisense-oligonucleotide works according to the invention so long as production of TGF-β is reduced or inhibited.

In a preferred embodiment of the present invention the antisense-oligonucleotide or effective derivative thereof is a phosphorothioate-oligodeoxynucleotide.

According to the invention the antisense-oligonucleotides are obtainable by solid phase synthesis using phosphite triester chemistry by growing the nucleotide chain in 3'-5' direction in that the respective nucleotide is coupled to the first nucleotide which is covalently attached to the solid phase comprising the steps of cleaving 5'DMT protecting group of the previous nucleotide, adding the respective nucleotide for chain propagation, modifying the phosphite group subsequently cap unreacted 5'-hydroxyl groups and cleaving the oligonucleotide from the solid support, followed by working up the synthesis product.

Figure 2:
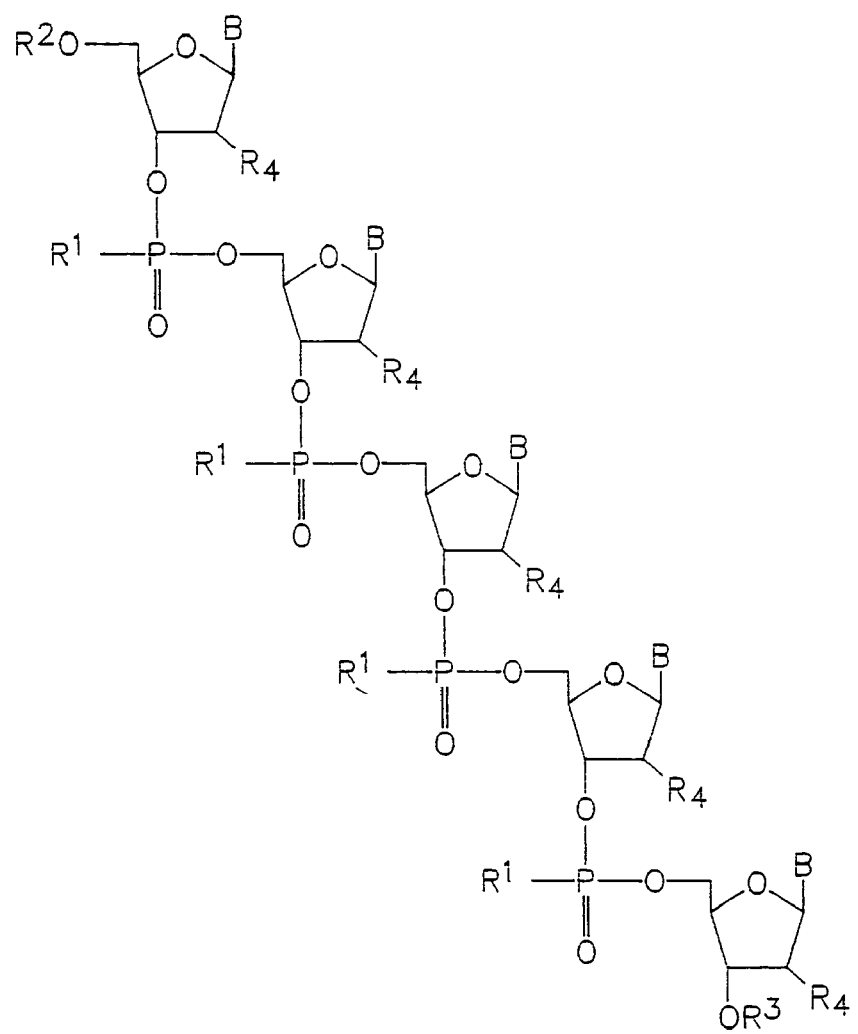
Figure 2:
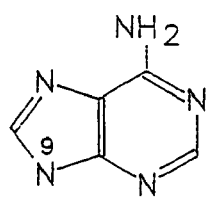
Figure 2:
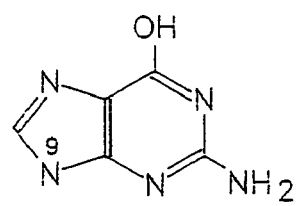
Figure 2:
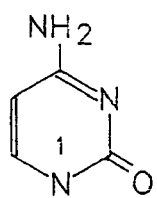
Figure 2:
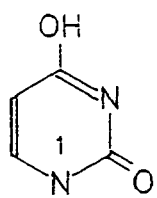

The chemical structures of oligodeoxy-ribonucleotides are given in FIG. 1 as well as the respective structures of antisense oligo-ribonucleotides are given in FIG. 2. The oligonucleotide chain is to be understood as a detail out of a longer nucleotide chain.

In FIG. 1 lit. B means an organic base such as adenine (A) guanin (G), cytosin (C) and thymin (T) which are coupled via N9(A, G) or N1(D, T) to the desoxyribose. The sequence of the bases is the reverse complement of the genetic target sequence (mRNA-sequence). The modifications used are 1. Oligodeoxy-ribonucleotides where all $R^1$ are substituted by

| | |
|---|---|
| 1.1 | $R^1 = O$ |
| 1.2 | $R^1 = S$ |
| 1.3 | $R^1 = F$ |
| 1.4 | $R^1 = CH_3$ |
| 1.5 | $R^1 = OEt$ |

2. Oligodeoxy-ribonucleotides where $R^1$ is varied at the internucleotide phosphates within one oligonuclectide $$5'\ \ B\text{-}p\text{-}B\text{-}p\text{-}B\text{-}p\text{-}(B\text{-}p\text{-})_n B\text{-}p\text{-}B\text{-}p\text{-}B\text{-}p\text{-}B\ \ 3'$$
$$\phantom{5'\ \ }|\ \ \ \ |\ \ \ \ |\ \ \ \ |\ \ \ \ \ \ \ \ \ |\ \ \ \ |\ \ \ \ |$$
$$\phantom{5'\ \ }R^{1a}\ R^{1a}\ R^{1a}\ R^{1a}\ \ \ \ R^{1a}\ R^{1a}\ R^{1a}$$

where B=deoxy-ribonucleotide dA, dC, dG or dT depending on gene sequence
p=internucleotide phosphate
n=an oligodeoxy-ribonucleotide stretch of length 6-20 bases

| | | |
|---|---|---|
| 2.1 | $R^{1a} = S;$ | $R^{1b} = O$ |
| 2.2 | $R^{1a} = CH_3;$ | $R^{1b} = O$ |
| 2.3 | $R^{1a} = S;$ | $R^{1b} = CH_3$ |
| 2.4 | $R^{1a} = CH_3;$ | $R^{1b} = S$ |

3. Oligodeoxy-ribonucleotides where $R^1$ is alternated at the internucleotide phosphates within one oligonucleotide $$5'\ \ B\text{-}p\text{-}(B\text{-}p\text{-}B\text{-}p)_n\text{-}B\text{-}p\text{-}B\ \ 3'$$
$$\phantom{5'\ \ }|\ \ \ \ |\ \ \ \ \ \ \ \ \ |\ \ \ \ |$$
$$\phantom{5'\ \ }R^{1a}\ R^{1b}\ R^{1a}\ R^{1b}$$

where B=deoxy-ribonucleotide dA, dC, dG or dT depending on gene sequence
p=internucleotide phosphate
n=an oligodeoxy-ribodincleotide stretch of length 4-12 dinucleotides

| | | |
|---|---|---|
| 3.2 | $R^{1a} = S;$ | $R^{1b} = O$ |
| 3.2 | $R^{1a} = CH_3;$ | $R^{1b} = O$ |
| 3.3 | $R^{1a} = S;$ | $R^{1b} = CH_3$ |

4. Any of the compounds 1.1-1.5; 2.1-2.4; 3.1-3.3 coupled at $R^2$ with the following compounds which are covalently coupled to increase cellular uptake

| | |
|---|---|
| 4.1 | cholesterol |
| 4.2 | poly(L)lysine |
| 4.3 | transferrin |

5. Any of the compounds 1.1-1.5; 2.1-2.4; 3.1-3.3 coupled at $R^3$ with the following compounds which are covalently coupled to increase cellular uptake

| | |
|---|---|
| 5.1 | cholesterol |
| 5.2 | poly(L)lysine |
| 5.3 | transferrin |

In the case of the RNA-oligonucleotides (FIG. 2) are the basis (adenin (A), guanin (G), cytosin (C), uracil (U)) coupled via N9 (A, G) or N1 (C, U) to the ribose. The sequence of the basis is the reverse complement of the genetic target sequence (mRNA-sequence). The modifications in the oligonucleotide sequence used are as follows 6. Oligo-ribonucleotides where all $R^1$ are substituted by

| | |
|---|---|
| 6.1 | $R^1 = O$ |
| 6.2 | $R^1 = S$ |
| 6.3 | $R^1 = F$ |
| 6.4 | $R^1 = CH_3$ |
| 6.5 | $R^1 = OEt$ |

7. Oligo-ribonucleotides where $R^1$ is varied at the internucleotide phosphates within one oligonucleotide $$5'\ \ B\text{-}p\text{-}B\text{-}p\text{-}B\text{-}p\text{-}(B\text{-}p\text{-})_n B\text{-}p\text{-}B\text{-}p\text{-}B\text{-}p\text{-}B\ \ 3'$$
$$\phantom{5'\ \ }|\ \ \ \ |\ \ \ \ |\ \ \ \ |\ \ \ \ \ \ \ \ \ |\ \ \ \ |\ \ \ \ |$$
$$\phantom{5'\ \ }R^{1a}\ R^{1a}\ R^{1a}\ R^{1b}\ \ \ \ R^{1a}\ R^{1a}\ R^{1a}$$

where B=ribonucleotide dA, dC, dG or dT depending on gene sequence
p=internucleotide phosphate
n=an oligo-ribonucleotide stretch of length 4-20 bases

| | | |
|---|---|---|
| 7.1 | $R^{1a} = S;$ | $R^{1b} = O$ |
| 7.2 | $R^{1a} = CH_3;$ | $R^{1b} = O$ |
| 7.3 | $R^{1a} = S;$ | $R^{1b} = CH_3$ |
| 7.4 | $R^{1a} = CH_3;$ | $R^{1b} = S$ |

8. Oligo-ribonucleotides where $R^1$ is alternated at the internucleotide phosphates within one oligonucleotide $$5'\ \ B\text{—}P\text{—}(B\text{—}p\text{—}B\text{—}p)\text{—}B\text{—}p\text{—}B\ \ 3'$$
$$\phantom{5'\ \ }|\ \ \ \ \ \ \ \ \ \ \ |\ \ \ \ \ \ \ \ \ \ \ |\ \ \ \ \ \ \ \ \ |$$
$$\phantom{5'\ \ }R^{1a}\ \ \ \ \ R^{1b}\ \ \ \ \ R^{1a}\ \ \ \ R^{1b}$$

where B=ribonucleotide dA, dC, dG or dT depending on gene sequence
p=internucleotide phosphate
n=an oligo-ribodinucleotide stretch of length 4-12 dinucleotides

| 8.2 | $R^{1a}$ = S; | $R^{1b}$ = O |
| 8.2 | $R^{1a}$ = CH$_3$; | $R^{1b}$ = O |
| 8.3 | $R^{1a}$ = S; | $R^{1b}$ = CH$_3$ |

9. Any of the compounds 6.1-6.5; 7.1-7.4; 8.1-8.3 coupled at $R^2$ with the following compounds which are covalently coupled to increase cellular uptake

| 9.1 | cholesterol |
| 9.2 | poly(L)lysine |
| 9.3 | transferrin |

10. Any of the compounds 6.1-6.5; 7.1-7.4; 8.1-8.3 coupled at $R^3$ the following compounds are covalently coupled to increase cellular uptake

| 10.1 | cholesterol |
| 10.2 | poly(L)lysine |
| 10.3 | transferrin |

11. Any of the compounds 6.1-6.5; 7.1-7.4; 8.1-8.3; 9.1-9.3; 10.1-10.3 where all $R^4$ are substituted by

| 11.1 | $R^4$ = O |
| 11.2 | $R^4$ = F |
| 11.3 | $R^4$ = CH$_3$ |

Modifications of the antisense-oligonucleotides are advantageous since they are not as fast destroyed by endogenous factors when applied as this is valid for naturally occurring nucleotide sequences. However, it is understood by the skilled person that also naturally occurring nucleotides having the disclosed sequence can be used according to the invention. In a very preferred embodiment the modification is a phosphorothioat modification.

The synthesis of the oligodeoxy-nucleotide of the invention is described as an example in a greater detail as follows.

Oligodeoxy-nucleotides were synthesized by stepwise 5'addition of protected nucleosides using phosphite triester chemistry. The nucleotide A was introduced as 5'-dimethoxytrityl-deoxyadenosine($N^4$-benzoyl)-N,N'-diisopropyl-2-cyanoethyl phosphoramidite (0.1 M); C was introduced by a 5'-dimethoxytrityl-deoxycytidine($N^4$-benzoyl)-N,N'-diisopropyl-2-cyanoethyl phosphoramidite; G was introduced as 5'-dimethoxytrityl-deoxyguanosine($N^8$-isobutyryl)-N,N'-diisopropyl-2-cyanoethyl phosphoramidite and the T was introduced as 5'-dimethodytrityl-deoxythymidine-N,N'-diisopropyl-2-cyanoethyl phosphoramidite. The nucleosides were preferably applied in 0.1 M concentration dissolved in acetonitrile.

Synthesis was performed on controlled pore glass particles of approximately 150 μm diameter (pore diameter 500 Å) to which the most 3' nucleoside is covalently attached via a long-chain alkylamin linker (average loading 30 μmol/g solid support).

The solid support was loaded into a cylindrical synthesis column, capped on both ends with filters which permit adequate flow of reagents but hold back the solid synthesis support. Reagents were delivered and withdrawn from the synthesis column using positive pressure of inert gas. The nucleotides were added to the growing oligonucleotide chain in 3'->5 direction. Each nucleotide was coupled using one round of the following synthesis cycle:

cleave 5'DMT (dimethoxytrityl) protecting group of the previous nucleotide with 3-chloroacetic acid in di chloromethane followed by washing the column with anhydrous acetonitrile. Then simultaneously one of the bases in form of their protected derivative depending on the sequence was added plus tetrazole in acetonitrile. After reaction the reaction mixture has been withdrawn and the phosphite was oxidized with a mixture of sulfur ($S_8$) in carbon disulfid/pyridine/triethylamine. After the oxidation reaction the mixture was withdrawn and the column was washed with acetonitrile. The unreacted 5'-hydroxyl groups were capped with simultaneous addition of 1-methylimidazole and acetic anhydryide/lutidine/tetrahydrofuran. Thereafter, the synthesis column was washed with acetonitrile and the next cycle was started.

The work up procedure and purification of the synthesis products occurred as follows.

After the addition of the last nucleotide the deoxynucleotides were cleaved from the solid support by incubation in ammonia solution. Exoxyclic base protecting groups were removed by further incubation in ammonia. Then the ammonia was evaporated under vacuum. Full-length synthesis products still bearing the 5'DMT protecting group were separated from shorter failure contaminants using reverse phase high performance liquid chromatography on silica $C_{18}$ stationary phase. Eluents from the product peak were collected, dried under vacuum and the 5'-DMT protecting group cleaved by incubation in acetic acid which was evaporated thereafter under vacuum. The synthesis products were solubilized in the deionized water and extracted three times with diethylether. Then the products were dried in vacuo. Another HPLC-AX chromatography was performed and the eluents from the product peak were dialysed against excess of Trisbuffer as well as a second dialysis against deionized water. The final products were lyophilized and stored dry.

The antisense-oligonucleotides of the invention can be used as pharmaceutical composition or medicament. This medicament can be used for treating tumors in which the expression of TGF-β is of relevance for pathogenicity by inhibiting the transforming growth factor-β and thereby reducing an immunosuppression and/or inhibiting pathological angiogenesis. The reduction of immunosuppression caused by the administration of an effective dose of an antisense TGF-β-oligonucleotides may be accompanied by an augmentated proliferation of cyctotoxic lymphocytes in comparison with the status before administration of the medicament. Thereupon, the lymphocytes are starting their cytotoxic activity decreasing the numbers of tumor cells.

The medicament of the present invention is further useful for the treatment of endogeneous hyperexpression of TGF-β, for treatment of rest tumors, for treatment of neurofibroma, malignant glioma including glioblastoma and for the treatment and prophylaxis of skin carcinogenesis as well as treatment of esophageal and gastric carcinomas.

The effect of TGF-$β_2$-specific antisense-oligonucleotides on human T cell proliferation and cytotoxicity upon stimulation with autologous cultured glioma cells was investigated. It was demonstrated that TGF-$β_2$-derived phosphorothioat-derivatives S-ODN's may specifically inhibit protein expression of TGF-β in glioma cells. In addition, TGF-$β_2$-specific S-ODN's revers—to a significant amount—immunosuppressive effects of TGF-β upon T-cell proliferation and cytotoxicity.

It has been shown that T-cell response in human brain tumor patients is clearly reduced and that tumor infiltrating lymphocytes have only marginal impact upon tumor progression of individual patients (Palma, L., Di Lorenzo, N., Guidett, B. Lymphocytes infiltrates in primary glioblastomas and recidivous gliomas, J. Neurosurg., 49: 854-861, 1978 and Ridley, A., Cavanagh, J. B. Lymphocytes infiltration in gliomas, Evidence of possible host resistance. Brain, 4: 117-124, 1971). Isolated tumor infiltrating lymphocytes from brain tumors are functionally incompetent, these immunosuppressive effects have been attributed to TGF-$\beta_2$ in vitro and in vivo (Bodmer, S., Stromer, K., Frei, K., Siepl, Ch., de Tribolet, N., Heid, I., Fontana, A., Immunosuppression and transforming growth factor-$\beta_2$ in glioblastoma, J. Immunol., 143: 3222-3229, 1989; Couldwell, W. T., Dore-Duffy, P., Apuzzo, M. L. J., Antel, J. P. Malignant glioma modulation of immune function: relative contribution of ifferent soluble factors, J. Neuroimmunol., 33: 89-96, 1991; Kuppner, M. C., Hamou, M. F., Sawamura, Y., Bodner, S., de Tribolet, N., Inhibition of lymphocyte function by glioblastoma derived transforming growth factor $\beta_2$, J. Neurosurg., 71: 211-217, 1989; Maxwell, M., Galanopoulos, T., Neville-Golden, J., Antoniades, H. N., Effect of the expression of transforming growth factor-$\beta_2$ in primary human glioblastomas on immunosuppression and loss of immune surveillance, J. Neurosurg., 76: 799-804, 1992; Palladino, M. A., Morris, R. E., Fletscher Starnes, H., Levinson, A. D., The transforming growth factor betas, A new family of immunoregulatory molecules, Ann. N.Y. Acad. Sci., 59: 181 to 187, 1990; Roszman, T., Elliott, L., Brooks, W., Modulation of T-cell function by gliomas, Immunol Today 12: 370-374, 1991).

FIG. 1: Chemical Structures of oligodeoxyribonucleotides.

FIG. 2: Structure of antisense oligo-ribobnucleotides.

Figure 3:
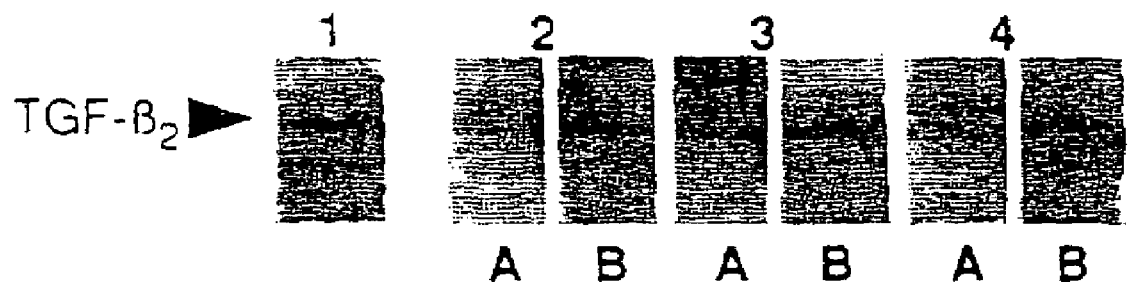

FIG. 3: IGF-$\beta$ western blot analysis of serum free glioma culture cell lysates. Lanes 2 (HTZ-153), 3 (HTZ-209), and 4 (HTZ-243) indicate blots of respective cell lysates with TGF-$\beta_2$ specific antibody. Lane 1 reprensents a TGF-$\beta$ positive control employing 50 ng pure TGF-$\beta_2$. TGF-$\beta_2$-antisense treated cells are displayed in lanes A. Untreated control cells are depicted in lanes B. Cells were treated with antisense oligonucleotides for 48 hrs (1 μM final concentration).

Figure 4:
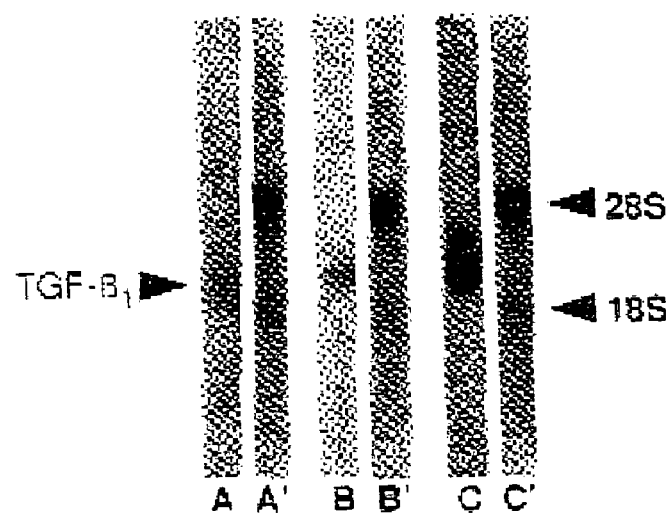

FIG. 4: TGF-$\beta_1$-mRNA expression in glioma cells. Each lane contained 20 μg of cytoplasmatic RNA from tumors A (HTZ-153), B (HTZ-209), C (HTZ-243) that hybridized to a $^{32}$P-labeled TGF-$\beta_1$ oligonucleotide probe. To verify equal amounts of RNA, the blot was stained with methylene blue prior to hybridization (lanes A', B', C').

Figure 5:
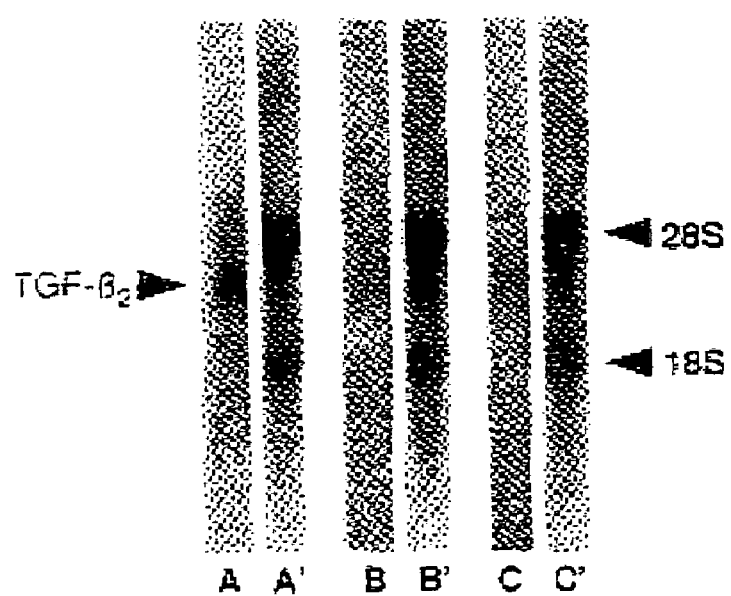

FIG. 5: TGF-$\beta_2$-mRNA expression in glioma cells. Each lane contained 20 μg of cytoplasmatic RNA from tumors A (HTZ-153), B (HTZ-209), C (HTZ-243) that hybridized to a $^{32}$p-labeled TGF-$\beta_2$ oligonucleotide probe. To verify equal amounts of RNA, the blot was stained with methylene blue prior to hybridization (A', B', C').

Figure 6:
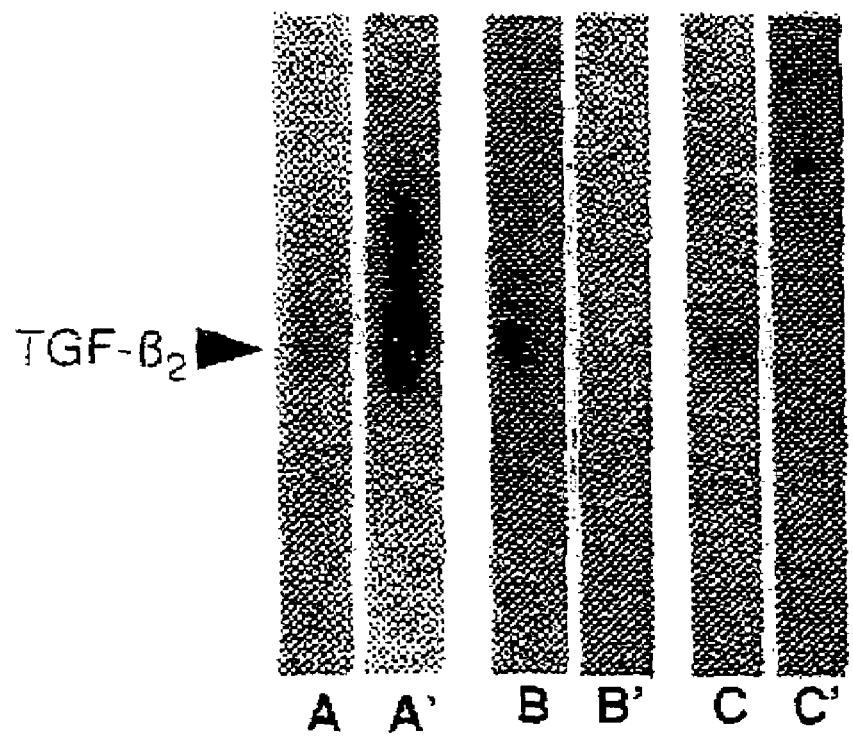

FIG. 6: TGF-$\beta_2$-mRNA expression in glioma cells after TGF-$\beta_2$-S-ODN treatment. Cytoplasmatic RNA of untreated glioma cells A (HTZ-153), B (HTZ-209) and C (HTZ-243) or glioma cells A', B' and C' treated for 48 hours with 1 μM (f.c.) TGF-$\beta_2$-specific S-ODN's under serum-enriched culture conditions, was isolated and processed for Northern blot analysis. Each lane contained 20 μg of cytoplasmatic RNA hybridized to a $^{32}$P-labeled TGF-$\beta_2$ oligonucleotide probe.

Figure 7:
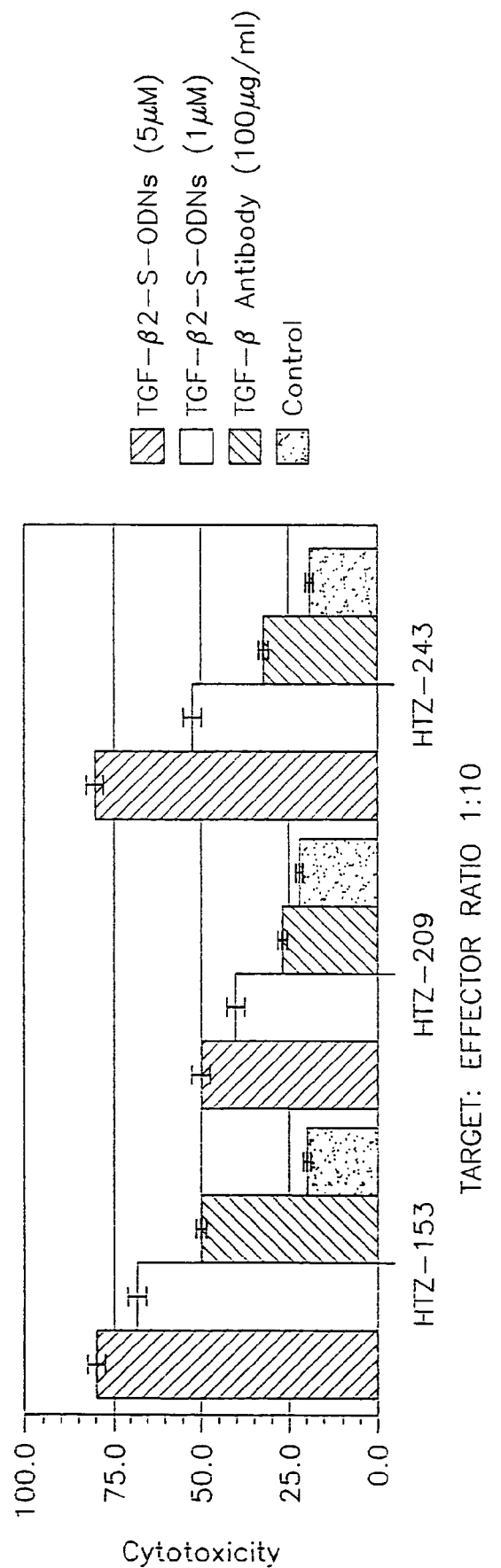

FIG. 7: Effect of TGF-$\beta_2$-specific S-ODN's and TGF-$\beta$ neutralizing antibody on cytotoxicity of PBMC's against autologous cultured glioma cells (target/effector 1:10). After 6 days culture of PBMC's with IL-1α and Il-2 the cells were collected, washed, irradiated (30 Gy) and added in target/effector ratios of 1:10, 1:5, 1:1 to autologous glioma cells. Glioma targets were pretreated with either TGF-$\beta$ specific S-ODN's or TGF-$\beta$ antibody. Cytotoxicity was assessed employing a modified microcytotoxicity assay. Data are means of triplicate samples, error bars represents SE. Data points reflect individual controls, where tumor targets were treated with medium alone (control). TGF-$\beta$ antibody (100 μg/ml), or S-ODN's (1 μM resp. 5 μM) as references for cytotoxicity effects. Thereby, effects upon target cells of antibody or S-ODN's alone could be excluded.

FIG. 8: Dose-dependent effects of TGF-$\beta_2$-specific and nonsense S-ODN's on proliferation of lymphocytes, glioma cells and lymphocytes cocultured with autologous glioma cells (MLTC). A: HTZ-153, B: (HTZ-209, C: HTZ-243. PBMC'x were preactivated for 6 days with IL-1α and IL-2 and incubated for additional 6 days with autologous irradiated (60 Gy) and TGF-$\beta_2$-(No. 6) and nonsense (no. 5) S-ODSN-treated glioma cells (MLTC). Simultaneously, part of preactivated PBMC's (lymphocytes) and glioma cells (tumor) were incubated with TGF-$\beta_2$ specific (Ly: No. 2, Tu: No. 4) and nonsense) S-ODN's (Ly: No. 1, Tu: No. 3) for 3 days, to evaluate putative direct effects of S-ODN's upon effector- or target cells alone. Proliferation of lymphocytes and glioma cells was assessed employing a $^3$H Tdr incorporation assay. Data are means of triplicate samples, error bars represent SE.

The invention is further explained by the following non-limiting examples.

EXAMPLE 1

Characterization of Tumor Cells (Autologous Target Cells)

Tumor cells of 3 patients with high grade malignant gliomas (HTZ-153 and HTZ 209, glioblastomas, HTZ-243, malignant astrocytoma, Gr.III-WHO) and their resp. autologous lymphocytes were studied. Standard tumor cell cultures were established in Dulbecco's Minimal Essential Medium containing 20% fetal calf serum (FCS, Seromed, Berlin, Germany), 1 μM L-glutamine, MEM vitamin solution and non-essential amino acids (GIBCO, Paisley, Scotland, U. K.) (Bogdahn, U., Fleischer, B., Rupniak, H. T. R., Ali-Osman, F. T-cell mediated cytotoxicity in human glioma Biology of Brain Tumor, Martinus Nijhoff Publishers, Boston, 70: 501-507, 1986). Other target cells included K562 (an NK-sensitive erythromyeloid leukemic cell line, American Type Culture Collection, Rockville, Md., USA). Tumor cell cultures were characterized by immunocytochemistry employing the PAP-method (Bourne, J. A., Handbook of immunoperoxidase staining methods, DAKO Corporation, Carpinteria Calif., USA, 1983) in Labtek tissue culture slides (Miles Laboratories Inc., Naperville, Ill., USA) with the following mono- or polyclonal antibodies to: GFAP, Cytokeratin, Neurofilament, Desmin, Vimentin, NSE, HLA, DrO, W6/32 (Class I Antigen), $\beta_2$-Microglobulin, Fibronectin, Laminin, Ki 67 (Dakopatts, Glostrup, Denmark) and anti-TGF-$\beta$ (R & D Systems, Inc., Minneapolis, Minn., USA). TGF-$\beta$ specific immunocytochemistry was performed after 48 hours incubation of glioma culture slides with 1 μM final concentration (f.c.) TGF-$\beta_2$-specific S-ODN's and 1 μM (f.c.) nonsense S-ODN's treated controls.

EXAMPLE 2

Characterization of Lymphocytes (Effector Cells)

Peripheral blood mononuclear cells from all glioma patients were isolated from heparinized venous blood at the day of surgery, employing Ficoll-Hypaque (Pharmacia, Uppsala, Sweden) gradient centrifugation and cryopreserved in liquid nitrogen under standard conditions (Bogdahn, U., Fleischer, B., Rupniak, H. T. R., Ali-Osman, F. T-cell mediated cytotoxicity in human glioma Biology of Brain Tumor, Martinus Nijhoff Publishers, Boston, 70: 501-507, 1986). Lymphocytes were cultured in RPMI 1640 (Flow Laboratories Inc., Scotland, U.K.) with 10% human pooled AB-serum (Flow Laboratories Inc. McLean, Va., USA) and 2 mM L-glutamine. Native and activated (see below) peripheral blood mononuclear cells were characterized by immunocytochemistry employing alkaline phosphatase and monoclonal anti-alkaline phosphatase complexes (APAAP-method, Dakopatts GmbH, Hamburg, Germany) (Cordell, J. L., Falini, B., Erber; W. N., et al., Immunoenzymatic labeling of monoclonal antibodies using immune complexes of alkaline phosphatase and monoclonal anti-alkaline phosphatase (APAAP complexes), J. Histochem. Cyto-chem., 32: 219-229, 1984) with monoclonal antibodies to the following antigens: CD3, CD4, CD8, CD16, CD25, HLA DR (Becton Dickinson, Mountain View, Calif. USA).

EXAMPLE 3

LAK-Cell Generation

As the proliferative and cytotoxic response of peripheral blood mononuclear cells from glioma patients is suppressed, cells ($2 \times 10^6$ cells/ml) were preactivated in vitro for 6 days with interleukin-1α (10 U/ml). R & D Systems, Inc., Minneapolis, Minn., USA) and interleukin-2 (100 U/ml), BIOTEST AG Frankfurt/M. Germany) in 48 flat bottom tissue culture plates ($2 \times 10^6$ cells/ml) (Costar, Cambridge, Mass., USA).

EXAMPLE 4

Proliferation Assay

In mixed lymphocyte-tumor cell cultures (MLTC) $15 \times 10^3$ lethally irradiated (60 Gy, $^{64}$Co-source) tumor cells served as stimulators, and were cocultivated with $25 \times 10^3$ pre-activated mononuclear cells (LAK-cells, see above) for 6 days in 96-well-flat bottom tissue culture plates (NUNC, Copenhagen, Denmark). In MLTC-experiments, the same culture medium conditions were employed as during preactivation. In antisense experiments, TGF-$\beta_2$-specific phosphorothioate oligodeoxynucleotides (S-ODN's) and nonsense oligodeoxynucleotides (see below) were added to the cultures 12 hours before MLTC assay. Anti-TGF-$\beta$ neutralizing antibodies (R & D Systems, Inc. Minneapolis, Minn., USA) were added to the culture 2 hours before MLTC.

EXAMPLE 5

Cytotoxicity Assay

Cytotoxicity experiments were performed with a modified microcytotoxicity assay (Bogdahn, U., Fleischer, B., Rupniak, H. T. R., Ali-Osman, F. T-cell mediated cytotoxicity in human glioma Biology of Brain Tumor, Martinus Nijhoff Publishers, Boston, 70: 501-507, 1986). Briefly, $1.5 \times 10^3$ target cells were seeded into 96-well flat bottom tissue culture plates. Twelve hours after plating, TGF-$\beta_2$-specific S-ODN's and nonsense oligodeoxynucleotides (anti-sense-controls) were added to the culture. Anti-TGF-$\beta$ neutralizing antibodies and normal rabbit serum (antibody-controls, R & D Systems, Inc. Minneapolis, Minn., USA) were added to the culture 22 hours after plating. Various ratios (target/effector ratio of 1:1, 1:5, 1:10 of preactivated effector cells (LAK-cells) were irradiated (30 Gy), and added to respective targets 24 hours after plating for 3 days under standard culture conditions (RPMI 1640 culture medium containing 10% pooled AB-serum and 2 μM L-Glutamine). No cytotokines were added to the culture during cytotoxicity experiments. An incubation period of 3 days was selected, as statistical evaluation of data turned out to be optimal at this time point. Killing of target cells was demonstrated by incorporation of Trypan blue dye (data not presented). Target cell proliferation in LAK-cell treated targets) was assessed with a standard $^3$H-Thymidine incorporation assay (6-$^3$ H-Thymidine, 1 μCi/well, spec. Activity 27 Ci/mmol). Liquid scintillation counting of $^3$H-thymidine incorporation was performed after 18 hours of incubation of cells. The specific cytotoxicity was calculated as:

$$(cpm_{(control)} - cpm_{(probe)}/cpm_{(control)}) \times 100\%.$$

EXAMPLE 6

Northern and Western Blot Analysis

Cytoplasmatic RNA was prepared by lysing glioma cells treated with 1 μM (f.c.) TGF-$\beta_2$ -specific S-ODN's for 48 hours and untreated controls in buffer containing 0.5% NP-40 (Sambrook, J., Fritsch, E. F., Maniatis, T Molecular cloning. A laboratory manual, 2nd Edition, Cold Spring Harbor Laboratory Press. 1989). For Northern hybridization aliquots of 20 μg denaturated RNA were separated by electrophoresis on 1% agarose-formaldehyd gel. The quality and quantity of immobilized RNA was verified by methylene-blue staining of the Hybond-N membranes (Amersham/Buchler, Braunschweig, Germany) after transfer. Blots were hybridized overnight with specific TGF-$\beta_1$- or TGF-$\beta_2$-synthetic oligonucleotide probes (40-mer, Oncogen Science, Seattle, USA), 5' labeled with (gamma-$^{32}$P)-ATP employing T4 polynucleotide kinase (Pharmacia, Freiburg, Germany) and exposed to X-ray film.

For Western blotting, TGF-$\beta$-S-ODN treated (48 hours, 1 μM f. c.) resp. untreated glioma cells were grown in medium containing 10% FCS washed and further cultured in defined serum free medium for 24 hours. The cells were lysed employing a lysis buffer containing NP-40. 30 μg of total cellular protein were loaded onto each lane of a 12% polyacrylamide-SDS gel. Fractionated proteins were then electroblotted to a nitrocellulose membrane for 20 minutes at 0.8 mA/cm$^2$ as described (Towbin, H., Staehelin, T., Gordon, J. Electrophoretic transfer of proteins from PAGE to nitrocellulose sheets: procedure and some applications, Proc. Natl. Acad. Sci., USA, 76: 4350-4354, 1979). Filters were probed with a polyclonal antibody of TGF-$\beta_2$ (R & D Systems Inc. Minneapolis, USA) 50 μg of TGF-$\beta$ served as control.

EXAMPLE 7

Phosphorothioate Modified Antisense Oligodeocynucleotides (S-ODN's)

TGF-$\beta_2$-specific antisense oligodeoxynucleotides (antisense direction of TGF-$\beta_2$ mRNA primer sequence oligonucleotide sequence: CAGCACACAGTAGT (SEQ ID NO: 138) and randomized nonsense sequence with the same GC-content as the specific S-ODN's (nonsense oligonucleotide sequence: GTCCCTATACGAAC (SEQ ID NO: 139)) were synthesized on an Applied Biosystems model 380 B DNA Synthesizer (Schlingensiepen, K.-H., Brysch, W. Phosphorothioate oligomers. Inhibitors of oncogene expression in tumor cells and tools for gene function analysis in: Erikson, R., Izant., J. (Eds.) Gene regulation by antisense nucleic acids. Raven Press New York 1992). S-ODN's were removed from the solid support with 33% ammonnia. Oligonucleotides still bearing the 5' trityl protecting group were purified by reverse phase HPLC, with an Aquapore RP-300, C8-column (Brownlee). Solvents: A-0.1 M TEAA pH 7, B-Acetonitrile. Gradient 3-35% B over 30 Min. linear. Trityl bearing fraction of oligonucleotides, corresponding to the full-length product were detritylated in 80% acetic acid/ETOH for 20 Min. extracted twice with diethyl-ether, desalted on a Sephadex G 25 (Pharmacia) column, ethanol precipitated (2×) and finally diluted in 0.1 M Tris/HCL pH 7.6. S-ODN's were judged from polyacrylamid-gel-electrophoresis to be more than 85% full-length material.

EXAMPLE 8

Characterization of Tumor Cells

All glioma cell cultures expressed GFAP, TGF-$\beta$, vimentin, and HLA-Class I antigens, as well as $\beta$-microglobulin, fibronectin, and KI 67, inconsistent expression was found with desmin, HLA-Class II antigen (positive: HTZ-209) and NSE (positive: HTZ-209, HTZ-243). No expression was found for cytokeratin, laminin and neurofilaments, indicating the glial origin of these tumor cells.

Western blot analysis of tumor cell lysates revealed that HTZ-153, HTZ-209 and HTZ-243 cells produced TGF-$\beta_2$ protein (FIG. 3).

Northern blot analysis of cytoplasmatic RNA's from all 3 tumors revealed message for TGF-$\beta_1$ (2.3 kB) and TGF-$\beta_2$ (4.1 kB) (FIGS. 5 and 5): message for TGF-$\beta_1$ was fairly well represented in all three tumors (FIG. 4), however, tumor HTZ-209 displayed a faint TGF-$\beta_2$ signal compared to the remaining tumors (FIG. 5).

EXAMPLE 9

Modulation of TGF-$\beta$ Expression by Treatment of Glioma Cells with TGF-$\beta_2$ Specific S-ODN's The effects of TGF-$\beta_2$-specific S-ODN-treatment upon TGF-$\beta_2$ mRNA- and -protein expression in glioma cells were analysed by Northern blotting. Western Blotting and immunocyto-chemistry. Northern blot analysis of glioma cells treated with TGF-$\beta_2$-specific S-ODN's (f.c. 1 $\mu$M for 48 hours) yielded inconsistent results: HTZ-153 displayed an increase in TGF-$\beta_2$-message, whereas tumors HTZ-209 and HTZ-243 showed no detectable message following antisense oligodeoxynucleotides treatment (FIG. 6). Western blot analysis revealed a decreased TGF-$\beta_2$-specific signal for all 3 tumors after S-ODN treatment (FIG. 3).

Immunostaining of glioma cultures treated with TGF-$\beta_2$-specific S-ODN's (f.c. 1 $\mu$M for 48 hours) revealed a decrease of TGF-$\beta$-dependant immunoreactivity compared to nonsense S-ODN-treated and untreated controls for all 3 tumors. Controls with normal mouse serum and human AB-serum were negative (slides not presented).

EXAMPLE 10

Characterization of Lymphocytes

Autologous effector lymphocytes employed in the following experiments on tumor defendant lymphocyte proliferation and glioma cytotoxicity were characterized by conventional lymphocyte differentiation antigens. Data or characterization experiments are displayed in table 1, cell populations reflect the phenotype of lymphocyte subsets of native (Day 0) and activated (Day 6) effector cells, employed in proliferation and cytotoxicity experiments. The percentage of $CD3^+$ cells increased during culture time, up to 85%. The same was true for $CD4^+$ (up to 80%). $CD8^+$ (up to 18), $CD25^+$ (up to 60%)-cells, the fraction of $CD16^+$ cells increased to a maximum of 50% (HTZ-243) during the first 6 days of culture.

EXAMPLE 11

Cytotoxicity Experiments

Native PBMC's of tumor-patients investigated in our study expressed low cytotoxic activity to autologous targets, (below 20% at target/effector ration 1:10. Preliminary experiments disclosed that preactivation of autologous effector PBMC's was most effective, when cells were incubated with 10 U/ML IL-1$\alpha$ adn 100 U/ml IL-2 for 6 days. These LAK-cells were employed in all further cytotoxicity/proliferation experiments.

At a target/effector ration of 1/10, LAK cells achieved a cytotoxic activity of up to 25% in the autologous target systems (FIG. 7). Preincubation of tumor cells with neutralizing TGF-$\beta$ antibodies (f.c. 100 $\mu$g/ml) resulted in a cytotoxicity of 30%-50% (5-30% increase above the untreated controls) (FIG. 7). When tumor cells were preincubated with TGF-$\beta_2$-specific antisense S-ODN's cytotoxicity increase in a dose dependent fashion to a maximum of 79% (5 $\mu$M S-ODN's, 25-60% increase above untreated controls) and 67% (1 $\mu$M S-ODNs, 15-45% increase above untreated autologous lymphocytes. All three effector cell populations expressed high NK-activity as detected by cytotoxicity assay against K 562 cell line, ranging from 60% to 75%.

EXAMPLE 12

Proliferation Experiments

Figure 8A:
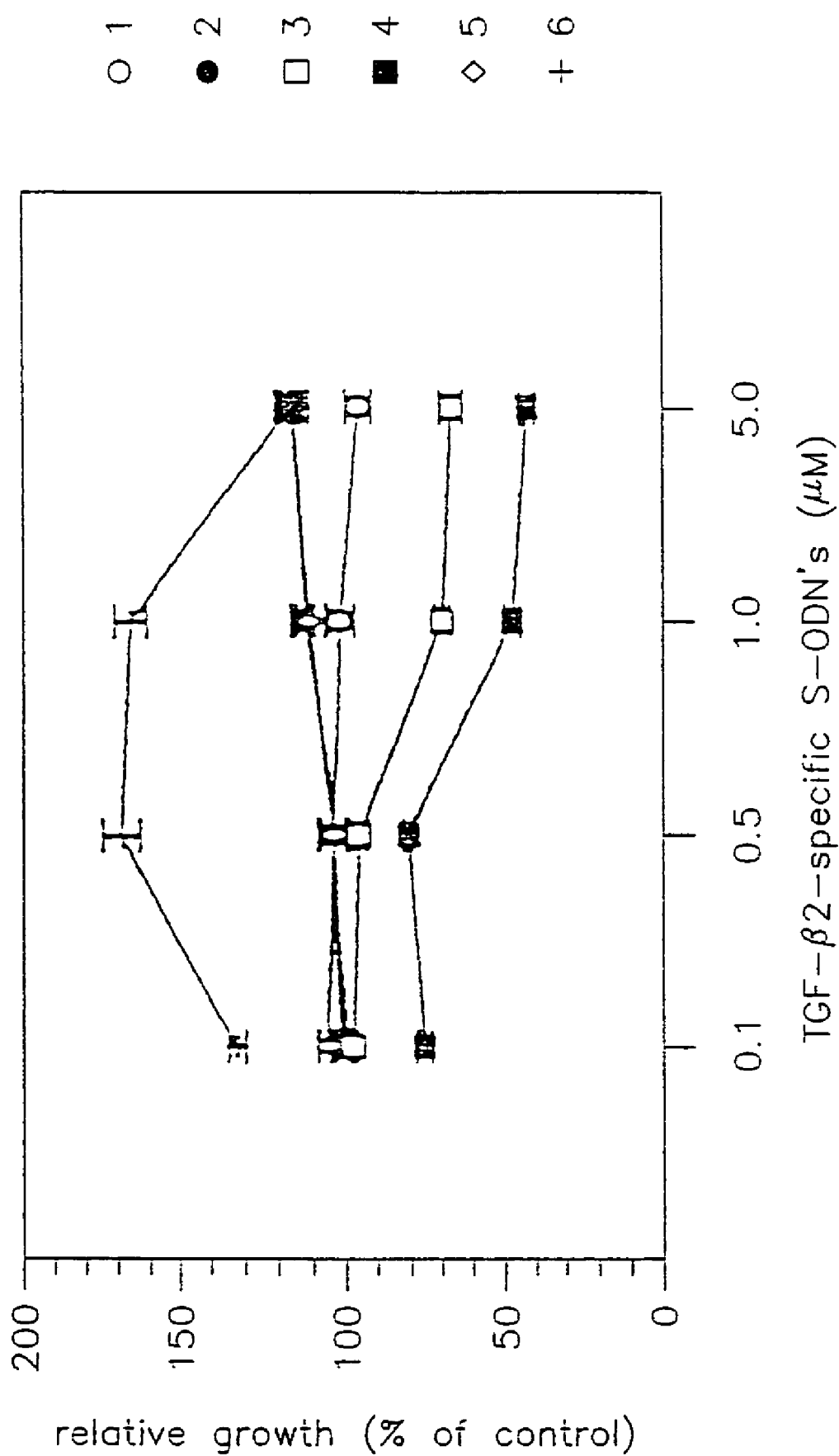
Figure 8B:
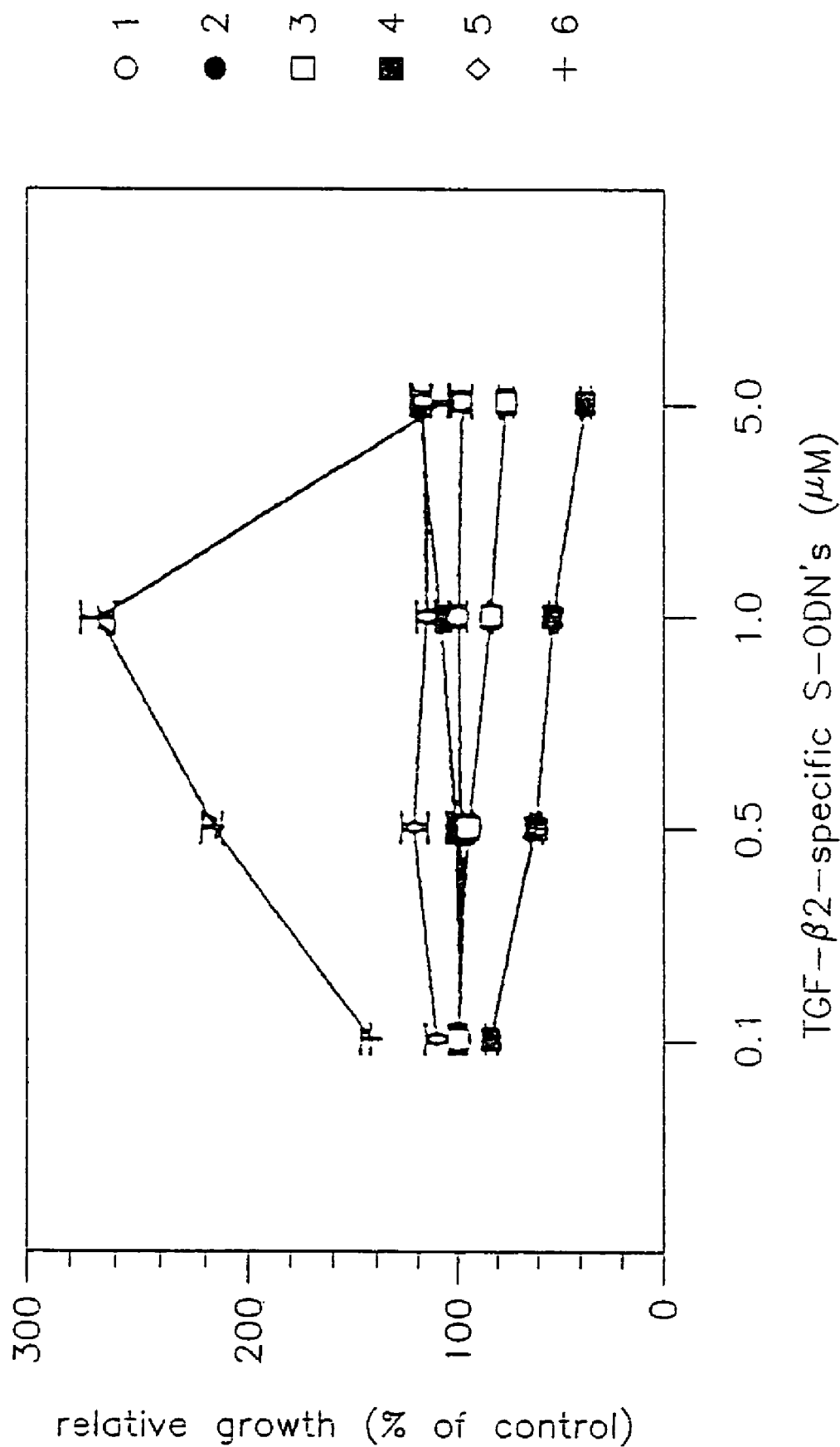
Figure 8C:
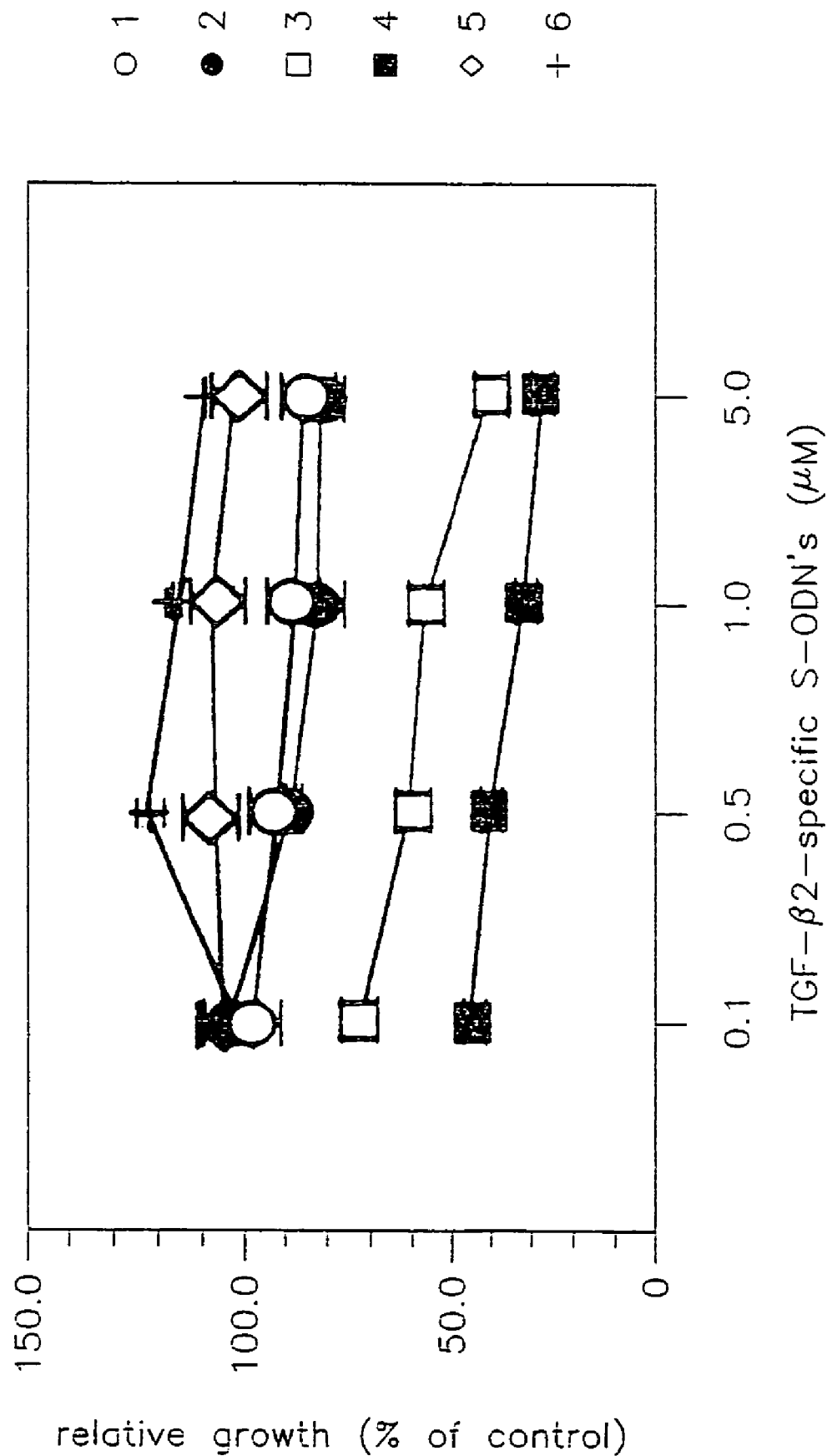

Lymphocyte proliferation upon stimulation with autologous tumor cells (MLTC) treated with TGF-$\beta_2$-specific S-ODNs was increased in tumors HTZ-153 (FIG. 8a) and HTZ-209 (FIG. 8b), however, no effect was observed in HTZ-243 cells (FIG. 8c) Nonsense S-ODN's at a final concentration (f.c.) of 1 $\mu$M did not alter lymphocyte proliferation (FIG. 8). Effects of TGF-$\beta_2$-specific S-ODN's were observed in a doese dependant fashion from 0.1 $\mu$M up to 1 $\mu$M, higher concentrations (5 $\mu$M) displayed non-specific toxicity towards PBMC's and tumor cells (FIG. 8): the proliferation of PBMC's in S-ODN treated MLTC's and tumor cells (FIG. 8):the proliferation of PBMC's in S-ODN treated MLTC's was persistently lower for oligonucleotide concentrations above 1 $\mu$M. High concentrations of neutralizing TGF-$\beta$ antibody (100 $\mu$g/ml) did not enhance lymphocyte proliferation. TGF-$\beta_2$-specific ant-sense S-ODN's had an inhibitory effect upon proliferation of either cultured lymphocyte populations (marginal effect) or autologous target cells (FIG. 8) achieving a maximum of 75% at a S-ODN's concentration of 5 $\mu$M (f.c.). Less profound inhibitory effects were observed with randomized control nonsense S-ODN's (average 20%, up to 40% at 5 $\mu$M f.c.).

The invention claimed is:

1. An antisense-oligonucleotide consisting of the nucleic acid sequence of SEQ ID NO: 83 or effective substituent-modified derivative thereof.

2. The antisense-oligonucleotide or effective substituent-modified derivative according to claim 1 obtained by solid phase synthesis using phosphite triester chemistry by growing the nucleotide chain in 3'-5' direction in that a respective nucleotide is coupled to the first nucleotide which is covalently attached to the solid-phase comprising the steps of cleaving 5' DMT protecting group of the previous nucleotide, adding the respective nucleotide for chain propagation, modifying phosphite groups and subsequently capping unreacted 5'-hydroxyl groups and cleaving the oligonucleotide from the solid support, followed by working up the synthesis product.

* * * * *

UNITED STATES PATENT AND TRADEMARK OFFICE
CERTIFICATE OF CORRECTION

PATENT NO.        : 7,667,027 B2                                              Page 1 of 1
APPLICATION NO. : 11/647586
DATED             : February 23, 2010
INVENTOR(S)       : Schlingensiepen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 103 days.

Signed and Sealed this

Twenty-eighth Day of December, 2010

David J. Kappos
*Director of the United States Patent and Trademark Office*